US006217873B1

(12) United States Patent
Rose et al.

(10) Patent No.: US 6,217,873 B1
(45) Date of Patent: *Apr. 17, 2001

(54) POLYOXIME COMPOUNDS AND THEIR PREPARATION

(75) Inventors: Keith Rose, Geneva; Robin E. Offord, Croix-de-Rozon, both of (CH)

(73) Assignee: Gryphon Sciences, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/537,928

(22) PCT Filed: May 5, 1994

(86) PCT No.: PCT/IB94/00093

§ 371 Date: Jan. 5, 1996

§ 102(e) Date: Jan. 5, 1996

(87) PCT Pub. No.: WO94/25071

PCT Pub. Date: Nov. 10, 1994

(51) Int. Cl.$^7$ ............... A61K 39/385; A61K 39/395; A61K 38/00; C07K 1/00
(52) U.S. Cl. ................... 424/193.1; 424/178.1; 424/194.1; 530/345; 530/391.1; 530/403; 530/404; 530/405; 530/406; 530/408; 530/409; 530/410
(58) Field of Search .................. 530/345, 403, 530/404, 405, 406, 408, 409, 410, 371.1, 391.1; 424/178.1, 193.1, 194.1

(56) References Cited

U.S. PATENT DOCUMENTS

| | | | |
|---|---|---|---|
| 4,444,744 | 4/1984 | Goldenberg | 424/1.1 |
| 4,507,466 | 3/1985 | Tomalia et al. | 528/332 |
| 4,622,420 | 11/1986 | Meares et al. | 562/443 |
| 4,652,440 | 3/1987 | Paik et al. | 424/1.1 |
| 4,659,839 | 4/1987 | Nicoloth et al. | 548/546 |
| 4,678,667 | 7/1987 | Meares et al. | 424/85 |
| 4,707,352 | 11/1987 | Stavrianpoulos | 424/1.1 |
| 4,857,599 | 8/1989 | Tomalia et al. | 525/259 |
| 4,861,581 | 8/1989 | Epstein et al. | 424/1.1 |
| 4,865,835 | 9/1989 | Begent | 424/1.1 |
| 4,918,164 | 4/1990 | Hellstrom et al. | 530/387 |
| 5,011,676 | 4/1991 | Thakur | 424/1.1 |
| 5,084,266 | 1/1992 | McKenzie et al. | 424/9 |
| 5,087,616 | 2/1992 | Myers et al. | 514/21 |

FOREIGN PATENT DOCUMENTS

| | | |
|---|---|---|
| 131 361 | 1/1985 | (EP) . |
| 243 929 | 11/1987 | (EP) . |
| 498 771 | 8/1992 | (EP) . |
| 525 992 | 2/1993 | (EP) . |
| 85/05638 | 12/1985 | (WO) . |
| 88/03414 | 5/1988 | (WO) . |
| 90/02135 | 3/1990 | (WO) . |
| 91/13097 | 9/1991 | (WO) . |
| 92/05802 | 4/1992 | (WO) . |

OTHER PUBLICATIONS

Altmann, K.H. & Mutter, M., "A General Strategy for the De Novo Design of Proteins–Template Assembled Synthetic Proteins", *Int. J. Biochem.*, vol. 22:947–956 (1990).

Antoni et al., "A Short Synthetic Peptide Fragment of Human Interleukin 1 With Immunostimulatory but not Inflammatory Activity", *J. Immunol.*, vol. 137:3201–3204 (1986).

Argos, P., "An Investigation of Oligopeptides Linking Domains in Protein Tertiary Structures and Possible Candidates for General Gene Fusion" *J. Mol. Biol.*, vol. 211:943–958 (1990).

Siegrist, et al., "Histochemistry of Receptors", *Prog.Histochem.Cytochem.*, vol. 26:110–118 (1992).

Biancalana et al., "Tactics and Strategies in Solid Phase Peptide Synthesis: New Directions, Methods and Applications", *Innovation and Perspectives in Solid Phase Synthesis*, R. Epton (ed.) Intercept Limited, pp. 135–152 (1992).

Brinkley, M., "A Brief Survey of Methods for Preparing Protein Conjugates With Dyes, Haptens, and Cross–Linking Reagents", *Biocong. Chem.*, vol. 3:2–13 (1992).

Brocklehurst and Little, "Reactivities of the Various Protonic States in the Reactions of Papain and of L–Cysteine with 2,2'– and with 4,4'–Dipyridyl Disulphide: Evidence for Nucleophilic Reactivity in the Unionized Thiol Group of the Cysteine–25 Residue of Papain Occasioned by its Interaction with the Histidine–159–Asparagine–175 Hydrogen–Bonded System", *Biochem.J.*, vol. 128:471–474 (1972).

Brown, et al., "Conservation of Determinants for Class II–Restricted T Cells Within Site E of Influenza Virus Hemagglutinin and Factors Influencing Their Expression", *J.Virol.*, vol. 67:2287–2893.

Canne, L.E., et al. "Total Chemical Synthesis of Unique Transcription Factor–Related Protein: cMyc–Max", *J. Am. Chem. Soc.*, vol. 117:2998–3007 (1995).

(List continued on next page.)

Primary Examiner—Keith D. MacMillan
Assistant Examiner—Maurie E. Garcia
(74) Attorney, Agent, or Firm—Liniak, Berenato, Longacre & White

(57) ABSTRACT

Provided by this invention are essentially homogeneous, defined compositions of matter and hetero-polyoximes of defined structure comprising a baseplate structure having a plurality of oxime bonds, wherein each oxime bond links a specifically active molecule to the baseplate. Also provided are novel baseplates having a plurality of oxime forming complementary reactive groups and novel specifically reactive molecules having an oxime forming complementary reactive group. Also provided by this invention are methods of preparing these novel compositions of matter by chemoselectively ligating via oxime bond formation a complementary orthogonal reactive group on the baseplate to a complementary reactive orthogonal group on a specifically active molecule. Methods of using these defined compositions of matter as well as pharmaceutical compositions comprising these defined compositions of matter and methods of their use are also provided by this invention.

17 Claims, 13 Drawing Sheets

OTHER PUBLICATIONS

Capon, et al., "Designing CD4 Immunoadhesins for AIDS Therapy", *Nature*, vol. 337:525–530 (1989).

Carlsson, J. et al., "Protein Thiolation and Reversible Protein–Protein Conjugation", *Biochem. J.*, vol. 173:723–737 (1978).

Dawson, P.E. and Kent, S.B.H., "Convenient Total Synthesis of a 4–Helix TASP Molecule by Chemoselective Ligation", *J. Amer. Chem. Soc.*, vol. 115:7263–7266 (1993).

Defoort et al., "A Rational Design of Synthetic Peptide Vaccine With a Built–in Adjuvant", *Chem. Abs.*, vol. 118:231792f (1993).

Defoort et al., "Complete Synthetic Vaccine With Built–in Adjuvant", *Peptides 1991*, J.E. Rivier (ed.) ESCOM Leiden, New York, pp. 845–846 (1992).

Drijfhout, J.W., and Bloemhoff, W., "A New Synthetic Functionalized Antigen Carrier", *Int. J. Peptide Protein Res.*, vol. 37:27–32 (1991).

Ernest et al., "Synthesis of A 4–Helix Bundle–Like Template–Assembled Synthetic Protein (TASP) by Condensation of a Protected Peptide on a Conformationally Constrained Cyclic Carrier", *Tetrahedron Letters*, vol. 31(28):4015–4018 (1990).

Fisch et al., "Site–specific Modification of Antibodies by Enzyme–assisted Reverse Proteolysis", *Peptides 1990*, E. Giralt & D. Andreu (eds.) ESCOM Science Publishers B.V., The Netherlands, pp. 819–821 (1991).

Floegel et al., "Molecular Dynamics Conformational Search of Six Cyclic Peptides Used in the Template Assembled Synthetic Protein Approach for Protein De Novo Design", *Biopolymers*, vol. 32:1283–1310 (1992).

Gaertner, H.F., et al., "Construction of Protein Analogues by Site–Specific Condensation of Unprotected Fragments", vol. 3:262–268 (1992).

Geoghegan, K.F., and Stroh, J.G., "Site–Directed Conjugation of Nonpeptide Groups to Peptides and Proteins via Periodate Oxidation of 2–Amino Alcohol. Application to Modification at N–Terminal Serine", *Bioconjugate Chem.*, vol. 3:138–146 (1992).

Geysen, H.M., and Mason, T.J., "Screening Chemically Synthesized Peptide Libraries for Biologically–Relevant Molecules", *Bioorganic & Med. Chem. Lett.*, vol. 3:397–404 (1993).

Hobbs et al., "Identification of a Lymphocyte–Activating Pentapeptide Sequence in the Fc Region of Human IgG1[1]", *J. Immunol.*, vol. 138:2581–2586 (1987).

Houghton et al., "Development of new Antimicrobial Agents Using a Synthetic Peptide Combinatorial Library Involving More Than 34 Million Hexamers", *Innovation and Perspectives in Solid Phase Synthesis*, R. Epton (ed.) Intercept Limited, Andover, pp. 237–239 (1992).

Houghton et al., "Generation and use of Synthetic Peptide Combinatorial Libraries for Basic Research and Drug Discovery", *Nature*, vol. 354:84–86 (1991).

Jackson, D.C. & Brown, L.E., "A synthetic Peptide of Influenza Virus Hemagglutinin as a Model Antigen and Immunogen", *Peptide Research*, vol. 4:114–124 (1991).

Jung et al, "Modern Methods in Multiple Peptide Synthesis and Multiple Peptide Analysis", *Solid Phase Synthesis* R. Epton (ed), Intercept, Andover, UK, pp. 227–235 (1992).

Kaneko et al., "New Hydrazone Derivatives of Adriamycin and Their Immunoconjugates–a Correlation Between Acid Stability and Cytotoxicity", *Biocong. Chem.*, vol. 2:133–141 (1991).

Kaumaya et al, "Template Vaccine Strategy Bypasses Haplotype–Restricted Immune Responses", *Peptides*, C.H. Schneider & A.N. Eberle (eds.) ESCOM Science Publishers B.V., Columbus, OH, pp. 139–141 (1993).

King et al. "Preparation of Protein Conjugates via Intermolecular Hydrazone Linkage", *Biochemistry*, vol. 25:5774–5779 (1986).

Kurth et al., "Site–Specific Conjugation of a Radioiodinated Phenethylamine Derivative to a Monoclonal Antibody Results in Increased Radioactivity Localization in Tumor", *J. Med. Chem.*, vol. 36:1255–1261 (1993).

Marsden and Subak–Sharpe, "Preparation of Branched Peptides in Assays for Antibodies", *Chem. Abs.*, vol. 118:234487w (1993).

Moore, J.S., "Carborod Molecular Scaffolding", *Nature*, vol. 361:118–119 (1993).

Mueller, et. al., "Antibody Conjugates with Morpholino-doxorubicin and Acid–Cleavable Linkers", *Bioconjugate Chem.*, vol. 1:325–330 (1990).

Murphy, A.M. et al., "Automated Synthesis of Peptide C–Terminal Aldehydes", *J. Amer. Chem. Soc.*, vol. 114:3156–3157 (1992).

Mutter et al., "The Construction of New Proteins: V.A. Template–Assembled Synthetic Protein (TASP) Containing Both a 4–Helix Bundle and β–Barrel–like Structure", *Proteins: Structure, Function & Genetics*, vol. 5:13–21 (1989).

Mutter et al., "Redesigning Peptide Structures: Side–Chain Assemblage on Topological Templates", *Peptides 1992*, C.H. Schneider & A.N. Eberle (eds.) ESCOM Science Publishers B.V., The Netherlands,pp. 87–88 (1993).

Nencioni et al, "In Vivo Immunostimulating Activity of the 163–171 Peptide of Human IL–1β", *J. Immunol.*, vol. 139:800–804 (1987).

Nyanguile, et al., Synthesis of Antiparallel 4α–helix Bundle TASP by Chemoselective Ligation, *Letters in Peptide Science*, vol. 1:9–16 (1994).

Offord, R. E., "Chemical Approaches to Protein Engineering", *Protein Design and the Dev. of New Therapeutics and Vaccines*, J.B. Hoof & G. Poste (eds.), The British Library, Plenum, New York, pp. 253–282 (1990).

Offord, R. E. "Chemical Approaches to Protein Engineering", *Protein Eng.: A Practical Approach*, Rees, A.R. et al., eds., Oxford Press, pp. 235–251.

Pochon et al., "A Novel Derivative of the Chelon Desferri-ozamine for Site–Specific Conjugation to Antibodies", *Int. J. Cancer*, vol. 43:1188–1194 (1989).

Posnett et al., "A Novel Method for Producing Anti–Peptide Antibodies: Production of Siste–Specific Antibodies to the T. Cell Antigen Receptor β–Chain", *The Journal of Biological Chem.*, vol. 263(4):1719–1725 (1988).

Rana et al., "Synthesis of A Metal–Ligating Amino Acid Suitable for Solid Phase Assembly of Peptides", *Tetrahedron Lett.*, vol. 33:4521–4524 (1992).

Reines, S.A. and Cantor, C.R., "New Fluorescent Hydrazide Reagents for the Oxidized 3'–terminus of RNA", *Nucleic Acids Res.*, vol. 1:767–786 (1984).

Roberts, et al., "Using Starburst Dendrimers as Linker Molecules to Radiolabel Antibodies", *Bioconjugate Chem.*, vol. 1(5):305–308 (1990).

Robey, F.A. and Fields, R.L., "Automated Synthesis of N'Bromoacetyl–Modified Peptides for the Preparation of Synthetic Peptide Polymers, Peptide–Protein Conjugates, and Cyclic Peptides", *Analytical Biochemistry*, vol. 177:373–377 (1989).

Rose, "Facile Synthesis of Artificial Proteins", *J.Amer.Chem.Soc.,* vol. 116:30–33 (1994).

Rose et al., "Attachment of Linker Groups to Carboxyl Termini Using Enzyme–Assisted Reverse Proteolysis", *Peptides 1988,* Jung & E. Bayer (eds.) Walter de Gruyter, Berlin—New York, pp. 274–276 (1989).

Rose et al., "Site–Specific Modification of Natural and Biosynthetic Polypeptides by Reverse Proteolysis", *Innovation and Perspectives in Solid Phase Synthesis,* R. Epton (ed.) Intercept., Andover, pp. 129–134 (1992).

Rose, Keith, "Artificial Proteins Made by Parallel Assembly", *Innovation and Perspectives in Solid Phase Synthesis,* R. Epton (ed.), pp. 21–28 (1994).

Ryser et al., "Colon Carcinoma Immunoscintigraphy by Monoclonal Anti–CEA Antibody Labeled with Gallium–67–Aminooxyacetyldeferroxamine", *J. Nucl. Med.,* vol. 33:1766–1773 (1992).

Schnolzer, M. and Kent, S.B.H., "Constructing Proteins by Dovetailing Unprotected Synthetic Peptides: Backbone–Engineered HIV Protease", *Science,* vol. 256:221–225 (1992).

Shao, J. and Tam, J.P., "Unprotected Peptides as Building Blocks for the Synthesis of Peptide Dendrimer with Oime, Hydrazone, and Thiazolidine Linkages", *Journal of Amer. Chem. Soc.,* vol. 117(14):3893–3899 (1995).

Tam, J.P., "Synthetic Peptide Vaccine Design: Synthesis and Properties of a High–Density Multiple Antigenic Peptide System", *Proc. Natl. Acad. Sci.,* vol. 85:5409–5413 (1988).

Tam et al., "Incorporation of T and B Epitopes of the Circumsporozoite Protein in a Chemically Defined Synthetic Vaccine Against Malaria", *J. Exp. Med.,* vol. 171:299–306 (1990).

Tam, J. & Zavala, F. "Multiple Antigen Peptide: A Novel Approach to Increase Detection Sensitivity of Synthetic Peptides in Solid–Phase Immunoassays", *J. Immunol. Methods,* vol. 124:52–61 (1989).

Tomalia et al., "Starburst Dendrimers: Molecular Level Control of Size, Shape, Surface Chemistry, Topology, and Flexibility from Atoms to Macroscopic Matter", *Angew. Chem. Int., Ed. Engl.,* vol. 29:138–175 (1990).

Trost, Barry M., "Reduction of C—N to CHNH by Metal Hydrides", *Comprehensive Organic Synthesis,* vol. 8:60–78 (1991).

Tuchscherer et al., "Protein De Novo Design: Condensation of Unprotected Peptide Blocks to Topological Templates via Selective Oxime Bond Formation", 13th American Peptide Symposium, Edmonton, Canada, Abst., p. 976 (Jun. 1993).

Tuchscherer, G., "Template Assembled Synthetic Proteins: Condensation of a Multifunctional Peptide to a Topological Template via Chemoselective Ligation", *Tetrahedron Letters,* vol. 34(2):8419–8422 (1993).

Vilaseca et al., "Synthesis and Use of a Defined Oligomer for Targeted Drug Therapy", *Peptides,* C.H. Schneider & A.N. Eberle (eds.) ESCOM Science Publishers B.V., Geneva, Switzerland, pp. 819–820 (1993).

Webb, et al., "Synthesis of 1–(Aminooxy)–4 [3–Nitro–2–Pyridyl)Dithio]Butane and1–(Aminooxy)–4–[3–Nitro–2–Pyridy)Dithiol]but–2–ene, Novel Heterobifunctional Cross–Linking Reagents", *Bioconjugate Chem.,* vol. 1:96–99 (1990).

Williams, R.E., "Monitoring Multiple Antigen (MAP) Syntheses and Peptide Reorientation on a new MAP Core", *Peptides,* C.H. Schneider & A.N. Eberle (eds.) ESCOM Science Publishers B.V. Canada, pp. 911–912 (1993).

```
          -COCH=NOCH₂CO-KLEEQRPERVKG-OH
          -COCH=NOCH₂CO-KLEEQRPERVKG-OH
CHCO-G G G K K K K K G-OH
          -COCH=NOCH₂CO-KLEEQRPERVKG-OH
   ‖
NOCH₂CO-KLEEQRPERVKG-OH
          -COCH=NOCH₂CO-KLEEQRPERVKG-OH
          -COCH=NOCH₂CO-KLEEQRPERVKG-OH
```

FIG. 1

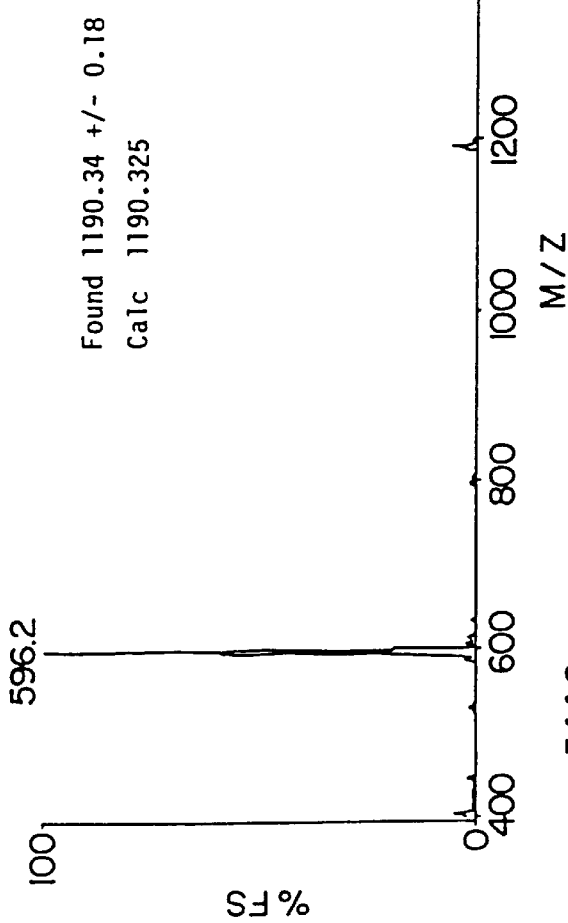
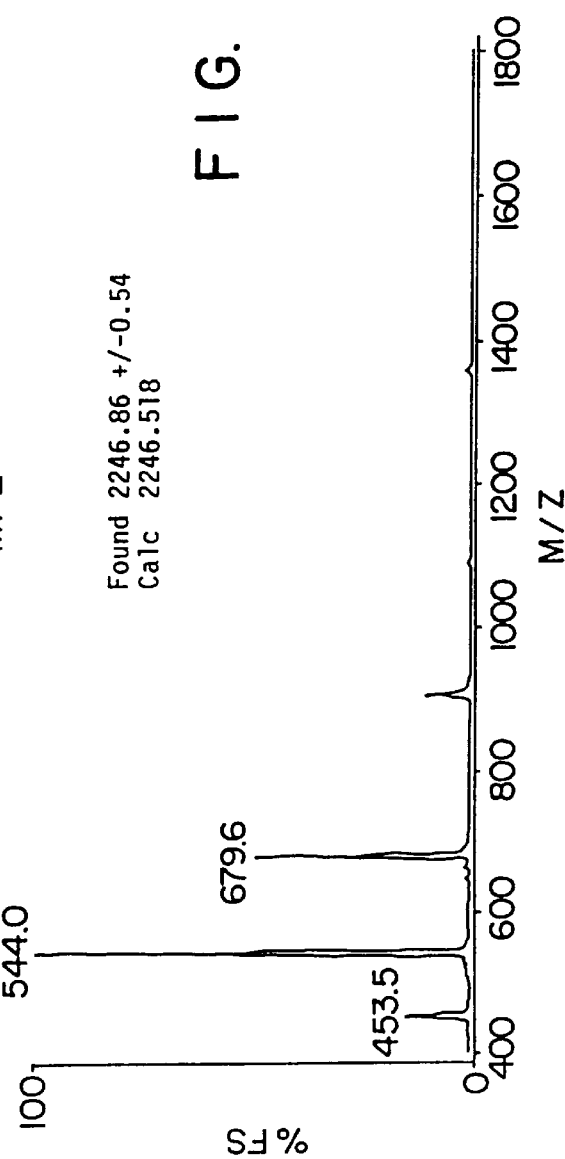
FIG. 12A
FIG. 12B

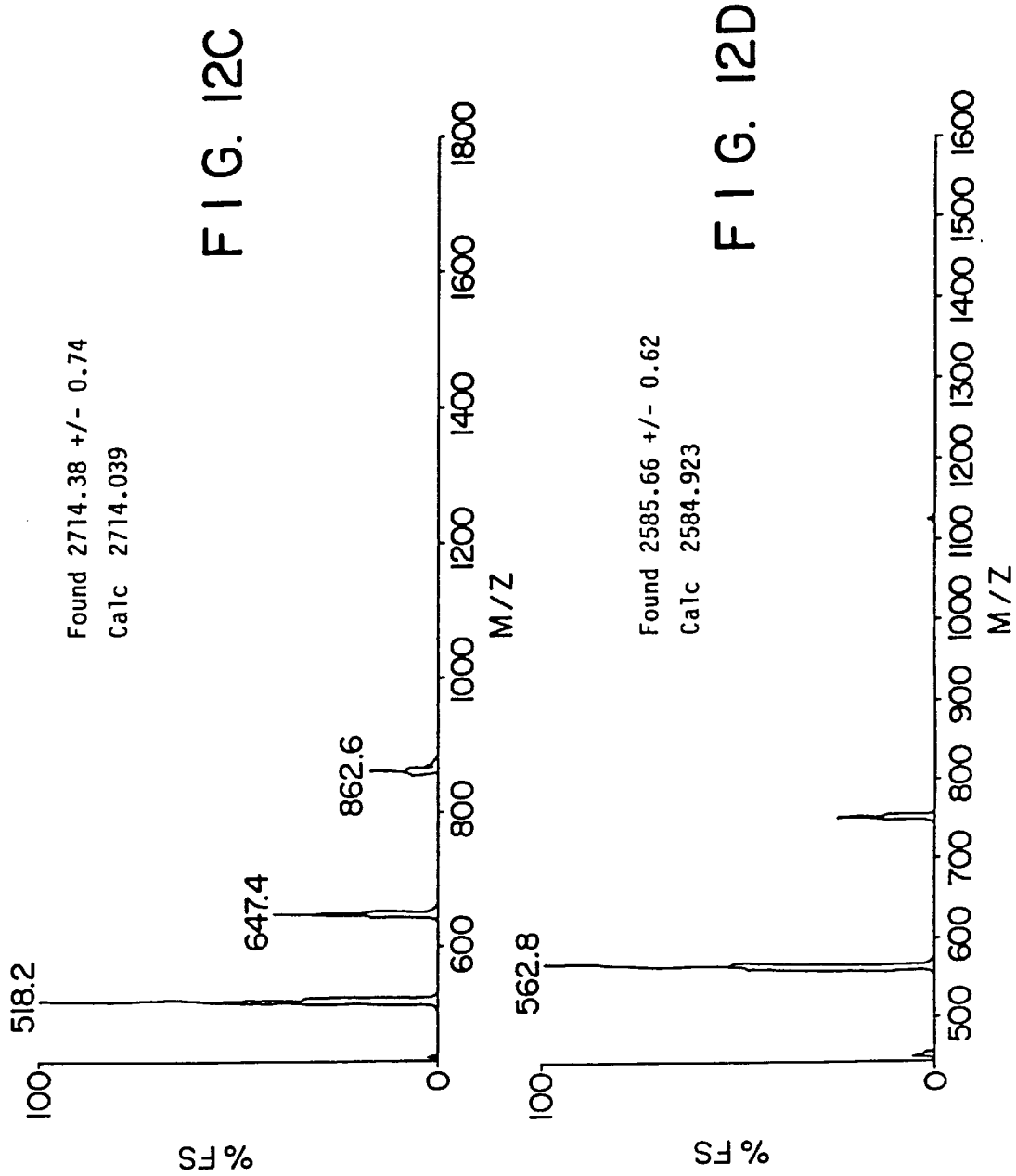

SEQUENCE LISTING

```
<160> NUMBER OF SEQ ID NOS: 30

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 1

Lys Leu Glu Glu Gln Arg Pro Glu Arg Val Lys Gly
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 2

Ser Lys Leu Glu Glu Gln Arg Pro Glu Val Lys Gly
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Lys

<400> SEQUENCE: 3

Xaa Leu Glu Glu Gln Arg Pro Glu Arg Val Lys Gly
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: GXL-Lys

<400> SEQUENCE: 4

Xaa Leu Glu Glu Gln Arg Pro Glu Arg Val Lys Gly
 1               5                  10
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Gly
<220> FEATURE:
<221> NAME/KEY: SITE
<222> LOCATION: (4)
<223> OTHER INFORMATION: Aminooxyacetyl-Lys
<220> FEATURE:
<221> NAME/KEY: SITE
<222> LOCATION: (5)
<223> OTHER INFORMATION: Aminooxyacetyl-Lys
<220> FEATURE:
<221> NAME/KEY: SITE
<222> LOCATION: (6)
<223> OTHER INFORMATION: Aminooxyacetyl-Lys
<220> FEATURE:
<221> NAME/KEY: SITE
<222> LOCATION: (7)
<223> OTHER INFORMATION: Aminooxyacetyl-Lys
<220> FEATURE:
<221> NAME/KEY: SITE
<222> LOCATION: (8)
<223> OTHER INFORMATION: Aminooxyacetyl-Lys

<400> SEQUENCE: 5

Xaa Gly Gly Xaa Xaa Xaa Xaa Xaa Gly
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: GXL-Gly
<220> FEATURE:
<221> NAME/KEY: SITE
<222> LOCATION: (4)
<223> OTHER INFORMATION: GXL-Lys
<220> FEATURE:
<221> NAME/KEY: SITE
<222> LOCATION: (5)
<223> OTHER INFORMATION: GXL-Lys
<220> FEATURE:
<221> NAME/KEY: SITE
<222> LOCATION: (6)
<223> OTHER INFORMATION: GXL-Lys
<220> FEATURE:
<221> NAME/KEY: SITE
<222> LOCATION: (7)
<223> OTHER INFORMATION: GXL-Lys
<220> FEATURE:
<221> NAME/KEY: SITE
<222> LOCATION: (8)
<223> OTHER INFORMATION: GXL-Lys

<400> SEQUENCE: 6

Xaa Gly Gly Xaa Xaa Xaa Xaa Xaa Gly
 1               5

<210> SEQ ID NO 7
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
<220> FEATURE:
<221> NAME/KEY: SITE
<222> LOCATION: (5)
<223> OTHER INFORMATION: Serine-Lys
<220> FEATURE:
<221> NAME/KEY: SITE
<222> LOCATION: (6)
<223> OTHER INFORMATION: Serine-Lys
<220> FEATURE:
<221> NAME/KEY: SITE
<222> LOCATION: (7)
<223> OTHER INFORMATION: Serine-Lys
<220> FEATURE:
<221> NAME/KEY: SITE
<222> LOCATION: (8)
<223> OTHER INFORMATION: Serine-Lys
<220> FEATURE:
<221> NAME/KEY: SITE
<222> LOCATION: (9)
<223> OTHER INFORMATION: Serine-Lys

<400> SEQUENCE: 7

Ser Gly Gly Gly Xaa Xaa Xaa Xaa Xaa Gly
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Bromoacetyl-Gly
<220> FEATURE:
<221> NAME/KEY: SITE
<222> LOCATION: (4)
<223> OTHER INFORMATION: GXL-Lys
<220> FEATURE:
<221> NAME/KEY: SITE
<222> LOCATION: (5)
<223> OTHER INFORMATION: GXL-Lys
<220> FEATURE:
<221> NAME/KEY: SITE
<222> LOCATION: (6)
<223> OTHER INFORMATION: GXL-Lys
<220> FEATURE:
<221> NAME/KEY: SITE
<222> LOCATION: (7)
<223> OTHER INFORMATION: GXL-Lys
<220> FEATURE:
<221> NAME/KEY: SITE
<222> LOCATION: (8)
<223> OTHER INFORMATION: GXL-Lys

<400> SEQUENCE: 8

Xaa Gly Gly Xaa Xaa Xaa Xaa Xaa Gly
 1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: GXL-Lys
<220> FEATURE:
<221> NAME/KEY: SITE
<222> LOCATION: (4)
<223> OTHER INFORMATION: GXL-Lys
```

```
<220> FEATURE:
<221> NAME/KEY: SITE
<222> LOCATION: (5)
<223> OTHER INFORMATION: GXL-Lys
<220> FEATURE:
<221> NAME/KEY: SITE
<222> LOCATION: (6)
<223> OTHER INFORMATION: GXL-Lys
<220> FEATURE:
<221> NAME/KEY: SITE
<222> LOCATION: (7)
<223> OTHER INFORMATION: GXL-Lys
<220> FEATURE:
<221> NAME/KEY: SITE
<222> LOCATION: (8)
<223> OTHER INFORMATION: GXL-Lys
<220> FEATURE:
<221> NAME/KEY: SITE
<222> LOCATION: (9)
<223> OTHER INFORMATION: GXL-Lys
<220> FEATURE:
<221> NAME/KEY: SITE
<222> LOCATION: (10)
<223> OTHER INFORMATION: GXL-Lys

<400> SEQUENCE: 9

Xaa Gly Gly Xaa Xaa Xaa Xaa Xaa Xaa Xaa Gly
 1               5                  10

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Glu

<400> SEQUENCE: 10

Xaa Leu Gly Gly Gly Pro Gly Ala Gly Ser Leu Gln Pro Leu Ala Leu
 1               5                  10                  15

Glu Gly Ser Leu Gln Lys Arg
            20

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (4)
<223> OTHER INFORMATION: GXL-Lys
<220> FEATURE:
<221> NAME/KEY: SITE
<222> LOCATION: (5)
<223> OTHER INFORMATION: GXL-Lys

<400> SEQUENCE: 11

Gly Gly Gly Xaa Xaa Gly
 1               5

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
<220> FEATURE:
```

```
<221> NAME/KEY: SITE
<222> LOCATION: (1)
<223> OTHER INFORMATION: Aminooxyacetyl-Tyr

<400> SEQUENCE: 12

Xaa Arg Glu Asp Gly Val Thr Pro Tyr Met Ile Phe Phe Lys Asp Gly
 1               5                  10                  15

Leu Glu Met Glu Lys
            20

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Lys

<400> SEQUENCE: 13

Xaa Leu Glu Gln Arg Pro Glu Arg Val Lys Gly
 1               5                  10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (2)..(6)
<223> OTHER INFORMATION: Xaa = Any Amino Acid

<400> SEQUENCE: 14

Gly Gly Xaa Xaa Xaa Xaa
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (2)..(6)
<223> OTHER INFORMATION: Xaa = Any Amino Acid

<400> SEQUENCE: 15

Gly Ala Xaa Xaa Xaa Xaa
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SIMILAR
<222> LOCATION: (2)..(6)
<223> OTHER INFORMATION: Xaa = Any Amino Acid

<400> SEQUENCE: 16

Arg Tyr Xaa Xaa Xaa Xaa
 1               5
```

```
<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (5)..(6)
<223> OTHER INFORMATION: Xaa = Any Amino Acid

<400> SEQUENCE: 17

Arg Tyr Gly Gly Xaa Xaa
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (5)..(6)
<223> OTHER INFORMATION: Xaa = Any Amino Acid

<400> SEQUENCE: 18

Arg Tyr Gly Ala Xaa Xaa
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (5)..(6)
<223> OTHER INFORMATION: Xaa = Any Amino Acid

<400> SEQUENCE: 19

Arg Tyr Lys Glu Xaa Xaa
 1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp
<220> FEATURE:
<221> NAME/KEY: SITE
<222> LOCATION: (13)
<223> OTHER INFORMATION: His-amide

<400> SEQUENCE: 20

Xaa Cys Thr Leu Ile Asp Ala Leu Leu Gly Asp Pro Xaa
 1               5                  10

<210> SEQ ID NO 21
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp
<220> FEATURE:
<221> NAME/KEY: SITE
<222> LOCATION: (2)
<223> OTHER INFORMATION: Cys (CH2CONH-CH2CH2NH-COCH2ONH2)-
<220> FEATURE:
<221> NAME/KEY: SITE
<222> LOCATION: (13)
<223> OTHER INFORMATION: His-amide

<400> SEQUENCE: 21

Xaa Xaa Thr Leu Ile Asp Ala Leu Leu Gly Asp Pro Xaa
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Asp
<220> FEATURE:
<221> NAME/KEY: SITE
<222> LOCATION: (13)
<223> OTHER INFORMATION: His-amide

<400> SEQUENCE: 22

Xaa Cys Thr Leu Ile Asp Ala Leu Leu Gly Asp Pro Xaa
 1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Asp
<220> FEATURE:
<221> NAME/KEY: SITE
<222> LOCATION: (2)
<223> OTHER INFORMATION: Cys (S-2-pyridyl)
<220> FEATURE:
<221> NAME/KEY: SITE
<222> LOCATION: (13)
<223> OTHER INFORMATION: His-amide

<400> SEQUENCE: 23

Xaa Xaa Thr Leu Ile Asp Ala Leu Leu Gly Asp Pro Xaa
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Cys
<220> FEATURE:
<221> NAME/KEY: SITE
<222> LOCATION: (10)
```

<223> OTHER INFORMATION: Cys-amide

<400> SEQUENCE: 24

Xaa Lys Ala Lys Pro Gly Lys Ala Lys Xaa
 1               5                  10

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic

<400> SEQUENCE: 25

Pro Lys Tyr Val Lys Gln Asn Thr Leu Lys Leu Ala Thr Gly Met Arg
 1               5                  10                  15

Asn Val Pro Glu Lys Gln Thr
            20

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Aminooxyacetyl-Pro

<400> SEQUENCE: 26

Xaa Lys Tyr Val Lys Gln Asn Thr Leu Lys Leu Ala Thr Gly Met Arg
 1               5                  10                  15

Asn Val Pro Glu Lys Gln Thr
            20

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp
<220> FEATURE:
<221> NAME/KEY: SITE
<222> LOCATION: (2)
<223> OTHER INFORMATION: Cys (CH2CH2CH2NH-Aminooxyacetyl)
<220> FEATURE:
<221> NAME/KEY: SITE
<222> LOCATION: (13)
<223> OTHER INFORMATION: His-amide

<400> SEQUENCE: 27

Xaa Xaa Thr Leu Ile Asp Ala Leu Leu Gly Asp Pro Xaa
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp

```
<220> FEATURE:
<221> NAME/KEY: SITE
<222> LOCATION: (2)
<223> OTHER INFORMATION: Cys (carboxamidomethyl)
<220> FEATURE:
<221> NAME/KEY: SITE
<222> LOCATION: (13)
<223> OTHER INFORMATION: His-NHCH2CH2NH-Aminooxyacetyl

<400> SEQUENCE: 28

Xaa Xaa Thr Leu Ile Asp Ala Leu Leu Gly Asp Pro Xaa
 1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp
<220> FEATURE:
<221> NAME/KEY: SITE
<222> LOCATION: (13)
<223> OTHER INFORMATION: His-NHCH2CH2NH-Aminooxyacetyl

<400> SEQUENCE: 29

Xaa Cys Thr Leu Ile Asp Ala Leu Leu Gly Asp Pro Xaa
 1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)
<223> OTHER INFORMATION: Acetyl-Asp
<220> FEATURE:
<221> NAME/KEY: SITE
<222> LOCATION: (2)
<223> OTHER INFORMATION: Cys (S-CH2CH2NHCOCH2ONH-Boc)
<220> FEATURE:
<221> NAME/KEY: SITE
<222> LOCATION: (13)
<223> OTHER INFORMATION: His-amide

<400> SEQUENCE: 30

Xaa Xaa Thr Leu Ile Asp Ala Leu Leu Gly Asp Pro Xaa
 1               5                   10
```

POLYOXIME COMPOUNDS AND THEIR PREPARATION

This application is the national stage under 35 U.S.C. §371 of International Application No. PCT/IB94/00093, filed May 5, 1994, which claims priority under 35 U.S.C. §365(c) to U.S. application Ser. No. 08/114,877, filed Aug. 31, 1993, and to U.S. application Ser. No. 08/105,904, filed Aug. 31, 1993, now U.S. Pat. No. 6,001,364 both of which are continuations-in-part of U.S. Ser. No. 08/057,594, filed May 5, 1993 now abandoned.

TECHNICAL FIELD

The invention relates generally to homogeneous preparations of polyoximes and to preparations of heteropolyoximes, said polyoximes being macromolecules of defined structure containing a plurality of oxime linkages, and to reagents and methods for assembly of such molecules.

BACKGROUND

Two methods have traditionally been used to produce complex polymers such as polypeptides. One method relies on relatively uncontrolled polymerization reactions, wherein monomer subunits react to produce large polymers. Using this method, polydisperse macromolecules such as polypeptides and plastics (e.g., polyethylene or nylon) can be produced from monomeric residues such as amino acids or small aliphatic or aromatic organic molecules, respectively. While such polydisperse macromolecules can be relatively easy to produce, the polymeric macroscopic products are not homogeneous at the molecular level but are mixtures of polymers of different lengths and even different composition, e.g., in a random copolymer. Furthermore, the similarity of the homologs produced in such polydisperse preparations makes it difficult or impossible to obtain a single high molecular weight product in pure form.

The second method utilized to obtain complex macromolecules has been the sequential assembly of reversibly protected monomers. This approach can be used to obtain products of defined, typically linear, structure. Unfortunately, the method is limited in the size and, most critically, the complexity of molecules that can be produced. For example, synthesis of defined polypeptides or proteins larger than about 50–80 amino acid residues has been beyond the reach of this technology. Condensation of prepurified protected peptides, two at a time, is limited by the insolubility of large protected fragments. As a result, synthesis of homogeneous, linear polypeptides, for example, is limited to an upper limit of about 100 amino acid residues.

Mutter et al. (Proteins:Structure, Function and Genetics (1989) 5:13–21) have synthesized branched chain polypeptides by step-wise coupling of protected amino acids to a synthetic, protected, resin-bound peptide template during solid-phase peptide synthesis. Deprotection and cleavage was required to obtain a soluble template-assembled synthetic protein. Also using step-wise, solid phase peptide synthesis, Tam and Zavala (J. Immunol. Meth. (1989) 124:5261) have built branched chain "lysine tree" templates with peptide branches, referred to as multiple antigen peptides, which were subsequently obtained in soluble, crude form after HF deprotection and cleavage.

Since protecting groups used in polypeptide synthesis generally decrease solubility of the protectable molecule, the ability to condense unprotected polypeptides would provide an improvement in the solubility problem encountered using protected precursors, as well as minimize harsh deprotection methods needed to achieve a final product. However, the use of unprotected precursors raises the seemingly insurmountable problem of regiospecificity. Therefore, attempts have been made to use regiospecific condensation of unprotected fragments through the use of chemoselective ligation.

Chemoselective ligation requires the use of complementary pairs of reactive groups present at specific sites on the precursor molecules that are being joined. The use of reactive groups having complementary chemical reactivity, such as a thiol group and a bromoacetyl group, results in the formation of a bond in a regiospecific manner. For example, thiol-type chemoselective ligations have been used to prepare multi-antigenic peptides. In an attempt to avoid harsh deprotection methods and formation of impure products caused by possible steric hindrance between closely spaced growing peptide arms during step-wise solid phase synthesis, Drijfhout and Bloemhoff (*Int. J. Peptide Protein Res.* (1991) 37:27–32) used thiol-type chemoselective coupling by synthesizing a branched "octa-amino lysine tree" peptide, whose deprotected amino groups were extended to contain protected sulfhydryl groups (S-acetylmercaptoacetyl) for subsequent coupling to an appropriately modified sulfhydryl-containing antigenic peptide. However, the product obtained had poor characteristics as defined by high performance liquid chromatography and was not fully characterized. More recently, thiol chemistry was used to prepare, in a two-fragment condensation, a totally synthetic, linear, functional HIV protease analog (Schnolzer and Kent (1992) Science 256:221–225).

Unfortunately, thiol chemistry is not completely specific. It is well known, for example, that thiol groups can participate in disulfide bond shuffling. In addition, alkylating agents such as bromoacetyl and maleoyl can react with nucleophilic amino acid groups other than a thiol group. For example, bromoacetyl can react with the thioether side chain of methionine residues, thus limiting the homogeneity and/or complexity of design of the desired product.

Thus, a need exists for preparations, particularly homogeneous preparations, of easily synthesized macromolecules of defined structure having stable ligation linkages and for reagents and methods for constructing these preparations of macromolecules that provide ease, rapidity and mildness of synthesis; essentially quantitative yields; versatility in design; and applicability to construction using a diversity of biochemical classes of compounds. In addition a need exists for macromolecules, particularly homogeneous macromolecules, of defined structure that can be designed for desired activity, solubility, conformation and other desirable properties; that present components, such as peptides or oligonucleotides, in non-linear, polyvalent form; that provide higher binding affinity and specificity of interaction; and, in the case of homogeneous macromolecules, can made available as homogeneous preparations. Furthermore the need exists for libraries of macromolecules such as peptides or oligonucleotides having advantages discussed herein, The present invention satisfies these needs and provides related advantages as well.

SUMMARY OF THE INVENTION

The present invention is directed to homogeneous preparations of easily synthesized, homogeneous macromolecules and to easily synthesized heterogenous macromolecules, said macromolecules being of defined structure and containing a plurality of stable oxime linkages and to reagents and methods for rapid and specific assembly of such macromolecules by chemoselective ligation via oxime formation.

The macromolecules of defined structure comprise an organic molecule (referred to as a baseplate) to which other molecules (referred to as COSMs) will be attached having a plurality of oxime linkages, preferably at least three, to a plurality of a second organic molecule (COSM).

In the case of homo-polyoxime macromolecules the COSMs are identical to each other. In one embodiment the oxime linkages are in the same orientation. In the case of hetero-polyoxime macromolecules, the baseplate is attached to a plurality of second organic molecules where at least one of the second organic molecules attached to the baseplate is different from the other attached second organic molecules. Also provided are two reagents for constructing these molecules: baseplates having a plurality of oxime-forming reactive groups and a second organic molecule having an orthogonal reactive group complementary in oxime linkage formation to the oxime forming orthogonal reactive groups present on the baseplate. For the purposes of the present invention, the second organic molecules are alternatively referred to as complementary orthogonal specifically active molecules ("COSM") and are defined further below. The oxime linkages provide a hydrolytically stable means of joining oligomer or macromolecule subunits. The various reactive groups are referred to herein as "orthogonal" groups, which means that they are complementary to each other in reactivity and do not react with other functional groups present in the precursors of the macromolecule being formed.

Also provided by this invention are methods of preparing these molecules, including by parallel self-assembly, comprising chemoselectively linking each of a plurality of orthogonal reactive groups on a baseplate to its complementary reactive orthogonal group present on one of a plurality of a second organic molecule via oxime bond formation. The baseplate and second organic molecules are preferably formed from amino acid residues. In other embodiments, baseplates and/or second organic molecules are formed from or further comprise sugar residues, nucleic acid residues and/or lipids. Preferred baseplates are prepared by controlled, organic chemical syntheses, such as solid phase peptide synthesis ("SPPS") or the equivalent for nucleic acids or carbohydrate-containing baseplates. Carbohydrate-containing baseplates are preferably isolated from natural or recombinant sources or prepared enzymatically. Homogeneous preparations of isolated peptides or proteins (prepared for example by recombinant means) are also suitable for use in making baseplate embodiments; however, such molecules must be designed or chosen to contain residues compatible with subsequent regio-specific modification to obtain a plurality of oxime-forming orthogonal reactive groups, and, in addition, maintain a defined structure and significant homogeneity after the regio-specific modification. Accordingly, heterogeneous antibody glycoprotein preparations subsequently modified by chemical or enzymatic oxidation of sugar residues are not suitable baseplate embodiments of the present invention.

Methods of using these polyoxime compounds are also provided, including use as antigens and immunogens. Compositions, including pharmaceutical compositions, comprising these compositions of matter are provided. Kits providing polyoximes of the invention or reagents for their synthesis are provided.

The polyoxime compounds of the invention are relatively complex, synthetically prepared macromolecules. The most massive species prepared to date is an approximately 20 kD complex, containing 195 amino acid residues: the homo-polyoxime octa-oxime formed between $NH_2OCH_2CO$-ELGGGPGAGSLQPLALEGSLQKR-OH (SEQ ID NO: 10) and O=CH-CO-Gly3-[Lys(COCHO)]7-Gly-OH (SEQ ID NO: 9). As will be apparent to those skilled in the art in the light of this disclosure, even larger and more complex molecules are now readily accessible in homogeneous and defined form given the rapid, specific, high-yielding, mild and versatile methods of preparing these compounds provided by this invention.

BRIEF DESCRIPTION OF THE DRAWINGS

FIG. 1 depicts the structure of the hexa-TCTP-polyoxime. As indicated, a TCTP-COSM is attached to each of the five e-positions of the lysine residues in the baseplate structure and to the N-terminus of the baseplate structure.

FIGS. 12A, 12B, 12C, and 12D depict mass spectrum and calculated molecular weights obtained by electrospray ionization mass spectrometry of four oxime products. FIG. 12A shows the spectrum of the mono-oxime formed between the baseplate terephthalaldehyde and the peptide $NH_2$ $OCH_2CO$-Nle-Asp-His-(D-Phe)-Arg-Trp-Lys-OH (a synthetic analog of alpha-melanocyte stimulating hormone ("MSH"). FIG. 12B shows the spectrum of the homo-polyoxime formed between the baseplate terephthalaldehyde and the peptide $NH_2$ $OCH_2CO$-Nle-Asp-His-(D-Phe)-Arg-Trp-Lys-OH. FIG. 12C shows the spectrum of the hetero-polyoxime (hetero-dimer) formed between the baseplate terephthalaldehyde and the peptides $NH_2$ $OCH_2CO$-Nle-Asp-His-(D-Phe)-Arg-Trp-Lys-OH and $NH_2$ $OCH_2CO$-Lys-Leu-Glu-Glu-Gln-Arg-Pro-Glu-Arg-Val-Lys-Gly-OH (SEQ ID NO: 4) FIG. 12D shows the spectrum of the hetero-polyoxime (hetero-dimer) formed between the base plate terephthalaldehyde and the peptides $NH_2OCH_2CO$-Nle-Asp-His-(D-Phe)-Arg-Trp-Lys-OH and $NH_2OCH_2CO$-Lys-Leu-Glu-Gln-Arg-Pro-Glu-Arg-Val-Lys-Gly-OH (SEQ ID NO: 13).

DETAILED DESCRIPTION OF THE INVENTION

Definitions

Figure 2:
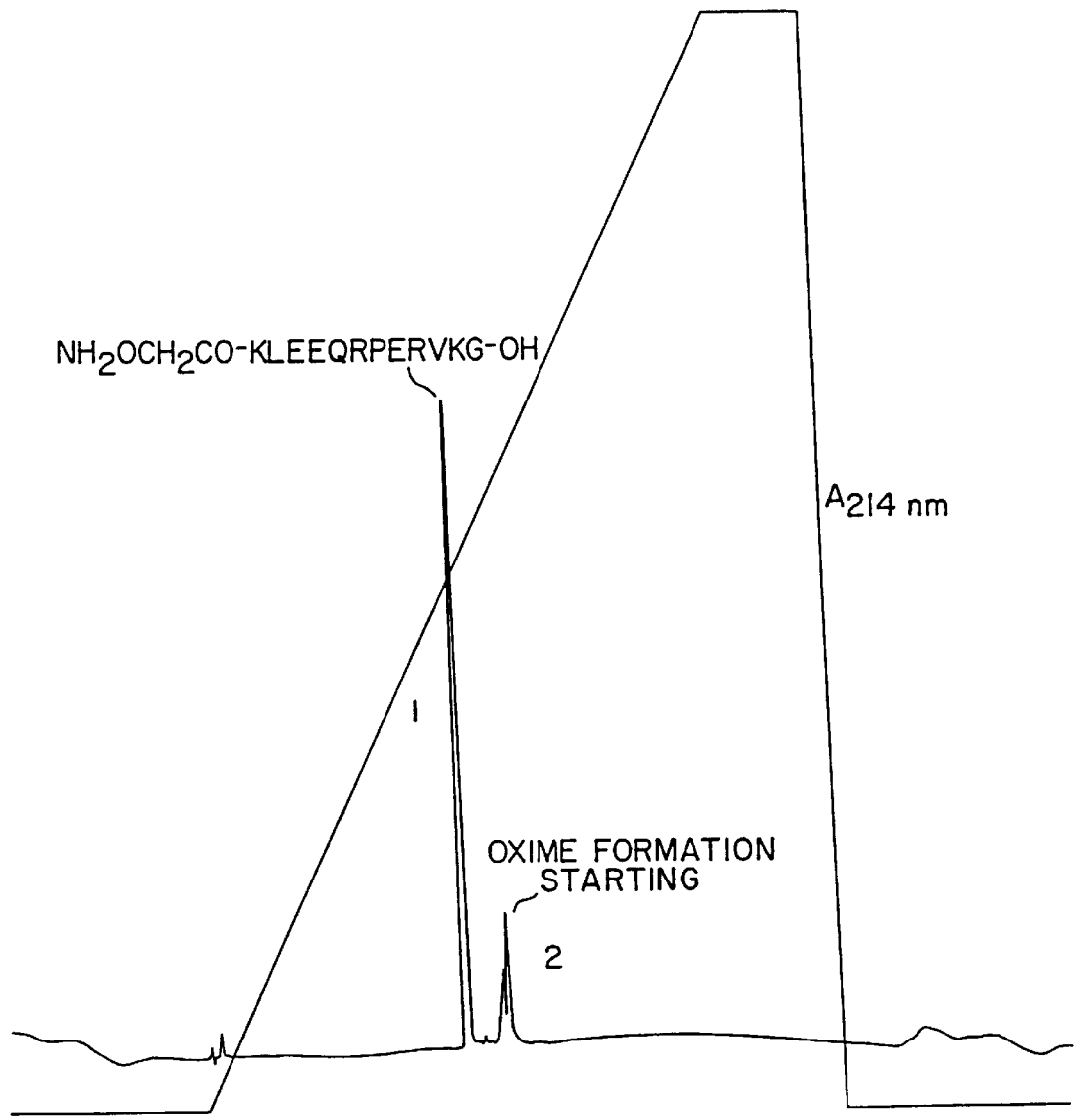
FIG. 2 shows the chromatogram obtained during RP-HPLC of a sample taken 3 hours after beginning the oximation reaction. Peak 1 indicates the fraction containing unbound TCTP-COSM, and Peak 2 indicates the fraction containing hexa-TCTP-polyoxime product.

For the purpose of this invention, the following terms are defined as follows.

A "complementary orthogonal chemically reactive group" is defined as one of a pair of chemically reactive groups that chemospecifically reacts with the complementary member of the pair. For example, amino-oxy-acetyl ("AOA") and glyoxylyl ("GXL") are complementary orthogonal chemically reactive groups that react to form an oxime bond.

The term "chemoselectively ligated" indicates the specific ligation that occurs between complementary orthogonal chemically reactive groups.

"Orthogonal" refers to conditions or groups which can be used without compromising other groups present or other chemistry to be applied. Thus, by way of example, in the context of this application, amino-oxy-acetyl groups are orthogonal.

A "complementary orthogonal specifically active molecule" ("COSM") is a molecule containing a complementary orthogonal chemically reactive group and a specifically active molecule or portion thereof. A COSM is defined in part by having a complementary orthogonal chemically reactive group capable of chemoselective ligation to the complementary orthogonal chemically reactive group present on a baseplate structure. For purposes of the present invention, the complementary orthogonal chemically reactive group of a COSM must be one member of an oxime-linkage-forming reactive pair. The term "specifically active" indicates that the COSM also has a defined biological, chemical or physical activity apart from its complementary orthogonal chemical reactivity. It is of course apparent that a defined, inherent activity for a COSM may not be immediately apparent from the COSM structure itself before reaction with the baseplate to form the final macromolecule product. As such the term COSM is not meant to limit the nature of the second organic molecules and is meant to be used interchangeably therewith. Furthermore, any specific activity associated with the second organic molecule can be activated or realized after attachment to the baseplate.

"Specific biological activity" means a biological activity imparted to a particular molecule or group by virtue of its structure. A specific biological activity can be unique to the particular molecule or group or can be associated with the members of a family to which the particular molecule or group belongs.

One skilled in the art would know that a specific biological activity also can be associated with structurally dissimilar or unrelated molecules or groups that possess the same specific biological activity as a particular molecule or group. For example, an anti-idiotypic antibody can have the same specific biological activity as the antigen used to raise the antibody to which the anti-idiotypic antibody was raised, even though the anti-idiotypic antibody and the antigen are structurally dissimilar.

"Specific chemical reactivity" means a chemical activity imparted to a particular molecule or group by virtue of its structure. A specific chemical activity can be unique to the particular molecule or group or can be associated with the members of a family to which the particular molecule or group belongs. Alternatively, a specific chemical activity can be associated with a small number of structurally dissimilar or unrelated molecules or groups that posses the same specific chemical activity as a particular molecule or group.

"Parallel assembly" means the multi-site, controlled reaction that occurs when a plurality of a second organic molecule (COSM) having one type of orthogonal chemically reactive group chemoselectively ligate to the complementary orthogonal chemically reactive groups on the baseplate structure.

An antigenic molecule encompasses a substance, frequently RNA or a peptide, that can stimulate an animal organism to produce antibodies and that can combine specifically with the antibodies thus produced. An antibody-antigen complex means a molecular aggregate that is formed by the specific interaction of antigens and antibodies.

An antibody is a glycoprotein of the globulin type that is formed in an animal organism in response to the administration of an antigen and that is capable of combining specifically with the antigen. These are also referred to as immunoglobulins. Antibody fragments can retain some ability to selectively bind with their antigen or hapten. The ability to bind with an antigen or hapten is determined by antigen-binding assays (see, for example, *Antibodies: A Laoratory Manual,* Harlow and Lane, eds., Cold Spring Harbor, New York (1988), which is incorporated herein by reference). Such antibody fragments include, but are not limited to, Fab, Fab' and (Fab')$_2$. A native antibody is one which is isolated from an animal or from an animal or hybrid animal (hybridoma) cell line.

A hapten refers to the portion of an antigen that reacts with the immune products of an immune response, but cannot by itself induce an immune response without being complexed to a carrier to form the complete antigen. Metal chelates are one example of a hapten.

As used herein, "complementarity determining region" (CDR) refers to amino acid sequences on either the variable light and variable heavy chain regions of an antibody which form a three-dimensional loop structure that contributes to the formation of the antigen or hapten binding site.

A therapeutic agent is any molecule, which, when administered to an animal, prevents or alleviates a disease or arrests or alleviates a disease state in the animal. Therapeutic agents may include, but are not limited to, antitumor antibiotics, antiviral proteins, radioisotopes, pharmaceuticals or a toxin.

A multivalent molecule is a molecule having more than one binding site for interaction between molecules. An example of a multivalent molecule is a polyvalent immunogen that contains multiple antigens.

A "pharmaceutically acceptable carrier" means any of the standard pharmaceutical carriers, such as a phosphate buffered saline solution; water; or emulsion, such as an oil/water emulsion; potentially including various types of wetting agents.

Administered means providing the subject with an effective amount of the compound or pharmaceutical composition. Methods of administration to an animal are well known to those of ordinary skill in the art and include, but are not limited to, oral, intravenous, transdermal, and parenteral administration. Administration may be effected continuously or intermittently throughout the course of other treatments. Methods of determining the most effective means and dosage of administration are well known to those of skill in the art and will vary with the compound or composition for treatment, the purpose of therapy and the animal or patient being treated.

A peptide or protein shall mean both naturally occurring and recombinant forms, as well as other non-naturally occurring forms of the peptide or protein which are sufficiently identical to the naturally occurring peptide or protein to allow possession of similar biological or chemical activity. As is known in the art peptides can be formed from of non-naturally occurring or non-proteinogenic amino acid residues. Furthermore, as is well known in the art, amino acid residues can be joined via non-amide linkages. Peptides or proteins can also contain protecting groups at either terminal that prevent or minimize degradation of the peptide or protein in vivo.

A "homogeneous polyoxime composition" of the invention refers to a chemical composition in which substantially all of the polyoxime molecules have identical chemical structures (in contrast to a typical organic polymer in which the individual molecules differ at least in length and often in specific structure, as in a random copolymer). Such compositions can also be referred to as "self-identical" compositions, as substantially all of the individual molecules of the polyoxime are identical to each other. Here "substantially all" refers to at least 80% of the total baseplate molecules all having the same number of identical COSMs attached to the baseplate. Increasing degrees of purity, such as 90%, 95%, 98%, 99%, 99.5%, 99.8%, etc., all the way to 100%, are increasingly preferred meanings of "substantially all." As discussed in the remainder of the application, for a hetero-polyoxime not all of the COSMs on a single baseplate will be identical, nevertheless the composition can be homogeneous as defined herein. As will be readily appreciated in light of the present invention, homogeneous polyoxime compositions can be comprised of homo-polyoximes or hetero-polyoximes. For example, step-wise assembly allows the introduction of a different COSM at each step to create a homogeneous composition of a hetero-polyoxime. Heterogeneous preparations of polyoximes can be deliberately produced by using a mixture of different COSMs during an oximation step, for example in creating a polyoxime peptide library or in attaching a COSM mixture comprised of molecules of a homologous series.

A "macromolecule" as used herein refers to an organic molecule (which includes molecules of biologic origin as well as organic molecules with inorganic components) having a molecular weight of at least 2000, preferably at least 5000, more preferably at least 10,000.

Description

This invention provides novel, multivalent molecules of defined structure comprising a plurality of stable oxime linkages, homogeneous compositions of these molecules, and reagents and methods for rapid and specific assembly of such molecules by chemoselective ligation via oxime formation. For purposes of this invention these molecules are referred to generally as polyoximes. Both homo-polyoximes and hetero-polyoximes are provided.

The homo-polyoxime compounds comprise an organic baseplate molecule having a plurality of oxime linkages, preferably at least three, to a plurality of a second organic molecule. In one embodiment all the oxime linkages are in the same orientation. The hetero-polyoxime compounds comprise an organic baseplate molecule having a plurality of oxime linkages, preferably at least three, to a plurality of second organic molecules; where at least one of the second organic molecules attached to the baseplate is different in chemical composition from another second organic molecule attached to the baseplate. Baseplates are organic molecules having a plurality of an oxime-forming orthogonal reactive group which can react chemoselectively with its complementary orthogonal reactive group present on any one of a plurality of a second organic molecule. Homogeneous compositions of polyoximes are formed by reaction via oxime bond formation of a complementary orthogonal reactive group on a baseplate to its complementary orthogonal reactive group on a second specifically active molecule. In a preferred embodiment of the invention, the baseplate structure is a peptide having a backbone formed from amino acid residues. As is known in the art, peptides containing non-naturally occurring amino-acids or D-optical isomers or substituted (e.g. N-substituted) amino acids, β-amino acids, or the like, can be made by chemical synthesis; peptides containing uncommon amino acids can be made by recombinant means but are usually produced by chemical synthesis or post-expression modification. The peptide baseplate backbone comprises amino acid residues having side-chain groups suitable for modification during peptide synthesis to oxime-forming complementary orthogonal reactive groups. Chemically reactive groups that can form oxime linkages with a complementary chemically reactive group on a COSM are present on preferably at least three of the amino acid residues in the baseplate. Amino acid residues can be incorporated during peptide bond formation as modified monomers containing oxime-forming chemically reactive groups or can be modified after formation of peptide bonds to contain such groups. Preferred common residues to carry oxime forming groups can be those which are available in differentially protected form, can easily be modified by conventional methods and which give stable derivatives. Preferred are lysine and ornithine residues, which are very easily acylated and can be modified by reductive alkylation, and cysteine residues, which can modified by alkylation or disulfide formation. Less preferred residues are serine, threonine, histidine, methionine (which can be alkylated), tyrosine (which can be alklylated but whose acyl derivatives are not very stable), and tryptophan (which can be alklylated or acylated). Residues can also be selected for conferring desired physical or biological properties, e.g., such as spacing, charge, solubility. Also preferred residues to carry an oxime forming group are homologs of these amino acids, D rather than L isomers, substituted derivatives (e.g. N-substituted), and β-amino acids.

In the case of hetero-polyoximes each chemoselectively ligated COSM on a baseplate can independently be the same or different from each other. Other embodiments contain baseplates and/or COSMs formed in whole or part from sugar residues, nucleic acid residues and/or lipids. As will be apparent from the disclosure of this invention, almost any oligo- or macromolecule building block residue can be used to form a COSM or a baseplate. As will be apparent to those skilled in the art in the light of this disclosure, even larger and more complex molecules are now readily accessible given the rapid, specific, high-yielding, mild and versatile methods of preparing these compounds.

In one embodiment the baseplate or COSM is designed and prepared by recombinant methods or isolated from natural sources, and an oxime-forming complementary orthogonal reactive group, such as an aldehyde, is site-specifically formed on the C-terminal of the polypeptide by selective enzyme catalyzed reverse proteolysis or at an N-terminal serine or threonine by mild oxidation. (See for example Geoghegan et al. (Bioconjugate Chem. (1992) 3:138–146), Gaertner et al. (Bioconjugate Chem. (1992) 3:262–268), EP 243929, and WO 90/02135 which are incorporated herein by reference.) For use as a multivalent baseplate a homogeneous preparation of recombinant or natural peptide preferably has multiple C- or N-termini, such as would occur in a dimer or tetramer, for ease of specific formation of orthogonally reactive groups. For example, an insulin analog having an A chain covalently linked to a B chain, each chain having an N-terminal serine (or threonine), can be converted to a divalent aldehyde baseplate by regio-selective oxidation. In a further embodiment, the C-termini can be modified by enzyme catalyzed reverse proteolysis to create a tri- or tetra-aldehyde baseplate. Such baseplates have at least the advantages of size and complexity over solid phase synthesis peptide baseplates. As is taught herein a great flexibility is available to one in the art for designing and obtaining baseplates and COSMs of desired sequence, structure and function with specifically placed complementary reactive groups. Polyoximes and methods for their synthesis developed in the laboratories of the present inventors described in Rose (J. Amer. Chem. Soc. "Facile synthesis of artificial proteins" (1994) 116:30–33; incorporated herein by reference).

Although the preferred baseplate and COSM structures are typically formed from amino acid residues, other embodiments include those formed from sugar residues, nucleic acid residues and/or lipids.

Where the baseplate or COSM structure is a peptide, the terminal chemical groups are normally an amino group and a carboxyl group. One skilled in the art will know that these terminal groups can be made reactive or unreactive. Unreactive groups can be unreactive because the group is chemically protected and can be made reactive by deprotecting or otherwise modifying the group as taught herein and as is known in the art. Alternatively, the terminal chemical groups of a baseplate can be covalently bonded to a residue within the baseplate structure to create a cyclic baseplate structure.

This invention provides in one embodiment a baseplate structure in which one complementary reactive group capable of oxime-linkage formation is an amino-oxy group or an aldehyde group. Preferred are amino-oxy-acetyl ("AOA") or aldehyde groups such as OHC—CO— or glyoxylyl ("GXL"). In fact, additional structure (X in the formula) can be used which connects an aldehyde group (or an amino-oxy group) to a structure of interest: e.g., OCH-X-Nle-Asp-His-(D-Phe)-Arg-Trp-Lys-OH, where X can simply be —CO— or a more elaborate structure; or NH$_2$-O-X-Nle-Asp-His-(D-Phe)-Arg-Trp-Lys-OH, where X can simply be —CH$_2$—CO— or a more elaborate structure.

When aldehyde groups are on the baseplate, groups present in the additional connecting structure adjacent to the aldehyde function are not critical; however, a requirement of these groups is that they do not interfere with the formation of the oxime linkage between the aldehyde and its complementary amino-oxy group. They should not react in preference to the aldehyde group with the amino-oxy, nor provide steric hindrance to the reaction, nor deactivate the reactive groups. The connecting group does not react with other functions present but if designed to do so then does not do so in an undesirable way (i.e., a way which reduces product homogeneity or activity).

The connecting group preferably represents a non-reacting group comprising substituted or unsubstituted aliphatic or aromatic groups such as phenyl or $C_1$–$C_{10}$ alkylene moieties, $C_1$–$C_{10}$ alkyl groups, or a combination thereof, or an amino acid chain (such as a flexible hinge or loop sequence (see for example Argos, J. Mol. Biol. (1990) 211:943–958), or a nucleotide chain or a sugar chain or a lipid chain or a combination thereof and may contain heteroatoms.

When amino-oxy groups are on the baseplate, functional groups present in the additional connecting structure adjacent to the amino-oxy function are not critical; however, a requirement of these linking groups is that they do not interfere with the formation of the oxime linkage between the amino-oxy and its complementary aldehyde group. They should not react in preference to the amino-oxy group with the aldehyde, nor provide steric hindrance to the reaction, nor deactivate the reactive groups.

The foregoing discussion describing functional groups present in the additional connecting structure adjacent to the aldehyde function or the amino-oxy function present on baseplates applies to connecting groups on COSMs.

Where the polyoxime is to be used for antigenic or immunogenic purposes, it is apparent to one skilled in the art that connecting groups are chosen that are not strongly immunogenic. Where the polyoxime is to be used for binding purposes, the preferred connecting group enhances or at least does not interfere with properties such as binding, avidity, product stability or solubility.

The connecting group can be chosen to enhance hydrolytic stability of the oxime linkage. The hydrolytic stability of oximes is influenced by their structure; data indicate that oxime stability increases in the series: —CO—NH—CH$_2$—CH=N—O—CH$_2$—<—NH—CO—CH=N—O—CH$_2$—<—C$_6$H$_4$—CH=N—O—(—H$_2$—.

The features of a connecting group also apply when baseplates and COSMs are made from sugar, nucleic acid or lipid residues.

Baseplates of the invention also optionally comprise residues that are not capable of forming oxime linkages with a COSM. Such residues can provide sufficient spacing between complementary reactive groups as to accommodate large COSMs. In addition such residues, when appropriately located, can provide other desirable features as are known or can be determined for sequences of such residues, including but not limited to providing desired tertiary conformation, conformational constraint, sidedness (as by formation of an amphipathic helix), scaffolding (as provided by engineered polypeptide minibodies), increased solubility, lipophilicity, biological activity or function. Examples of such chemically inert residues include but are not limited to amino acids, sugars and nucleotides. One skilled in the art is well aware of the various methods for predicting secondary and even tertiary structure of complex molecules techniques which are applicable to designing baseplate embodiments of the invention having desired functionality.

Where the baseplate structure comprises a peptide, one skilled in the art would know that the peptide baseplate structure will have a conformation in solution that depends in part on the amino acid sequence of the peptide. Such information is useful in determining an optimal amino acid sequence of the peptide baseplate structure for a specific task. For example, a peptide baseplate structure that is predicted to form an a-helix structure can be synthesized such that the amino acid residues that contain the complementary orthogonal chemically reactive groups extend from the same face of the a-helix. Following chemoselective ligation with a COSM, the specifically active region of each COSM will extend in the same direction. One skilled in the art knows of other types of conformations assumed by specific peptides in solution and therefore can synthesize polyoximes having desired tertiary structure, including desired spacing between adjacent COSMs. For example, preferred synthetic peptide baseplates, peptide design methods, and other synthetic considerations are exemplified in part by Altmann and Mutter (*Int. J. Biochem.* (1990) 22:947–956) and references cited therein.

A "lysine tree" formed by solid phase peptide synthesis as illustrated by Tam and Zavala (*J. Immunol. Meth.* (1989) 124:52–61), which is incorporated herein by reference, is suitable for use in baseplate formation if modified as described herein to contain oxime-forming complementary orthogonal reactive groups, which can be in the same orientation. Alternatively, a baseplate structure can be formed from a template such as used for "template assembled synthetic protein" ("TASP") described, for example, by Floegel et. al. (*Biopolymers* (1992) 32:1283–1310), which is incorporated herein by reference, if modified as described herein to contain oxime forming complementary orthogonal reactive groups, which can be of the same orientation. Aldehyde or amino-oxy end-functionalized carborods can serve as di-valent baseplates or alternatively COSMs. Carborods, which are prepared as homogeneous molecules of discrete length and defined structure, can be modified with specific end-group functionality. (See Moore, (1993) Nature 361:118–119, and references cited therein, which are incorporated by reference.)

When the baseplate is formed from amino acids, the peptide sequence of a baseplate structure can be synthesized by routine solid phase peptide synthesis ("SPPS") and, while the peptide is still attached to the solid phase, Boc-amino-oxyacetic acid (Boc-AOA) in an activated form such as the N-hydroxysuccinimide ester can be added to the nascent peptide chain. For example, the baseplate structure can consist of a peptide having five reactive groups such as five lysine residues. Boc-AOA N-hydroxysuccinimide ester can react with each of the e-amino groups of the lysine residues, as well as the N-terminus a-amino group if left unprotected, to form the baseplate structure which, in this example, would contain an ε-AOA-pentalysine sequence and an AOA group at the N-terminus, if the N-terminus α-amino group was intentionally acylated.

Alternatively, Boc-Ser(benzyl)—OH or Boc-Ser(t-butyl)—OH in an activated form such as the N-hydroxysuccinimide ester can be used to form the complementary orthogonal chemically reactive group on the baseplate structure. Boc-serine(benzyl) N-hydroxysuccinimide ester reacts with the e-amino groups of the five lysine residues, as well as the N-terminus α-amino group if desired, to form a precursor baseplate containing ε-Ser-pentalysine and an N-terminus α-Ser group. Treatment of the precursor baseplate with a mild oxidizing agent, such as periodate at pH 7, will convert ε-Ser-pentalysine and, if present, the α-Ser-N-terminus to ε-GXL-pentalysine and an α-GXL-N-terminus, respectively, thus producing a hexa-GXL-baseplate structure.

The oxidation reaction can be terminated using any 1,2-diol or 1-amino-2-ol or 1-ol-2-amino compound having relatively free rotation about the 1,2 bond, such as ethylene glycol. Alternatively, the oxidation reaction can be terminated by rapid removal of periodate, for example by reverse phase high performance liquid chromatography (RP-HPLC). Since the oxidation reaction only occurs with serine residues containing a primary amino group, only the ε-serine residues and serine residues at the N-terminus of the peptide are converted to the glyoxylyl. One skilled in the art knows of methods for chemically protecting an N-terminal serine from oxidation, if such protection is desirable.

Following conversion of the ε- and α-serine residues to GXL groups, an oximation reaction can occur between the GXL-baseplate structure and complementary AOA-COSMs at pH 4.6 to form a polyoxime. Oximes form over a wide range of pH values and form rapidly at pH values less than about pH 5. The extent of polyoxime formation can be monitored by RP-HPLC and the reaction can be terminated by preparative RP-HPLC. The molecular weight of the resulting compound can be determined by electrospray ionization mass spectrometry. Alternatively, an AOA-baseplate structure can be used, and an oximation reaction can occur between the AOA-baseplate structure and a plurality of a COSM having an aldehyde group.

Alternatively, oximation is run at pH below 4.6. Lower pH can be advantageous for the solubility of some peptides. A pH of 2.1 is preferred for increasing the solubility of some peptides, e.g. amino-oxy-acetyl-YREDGVTPYMIFFKDGLEMEK—OH (SEQ ID NO: 12). In addition oximation occurs much faster at pH 2.1 than at pH 4.6. One skilled in the art can determine the pH versus solubility profile of a COSM and a baseplates for polyoxime formation and choose an appropriate pH for a specific oximation reaction, taking into account pH stability of the molecules during the period of the oximation reaction.

The complementary orthogonal chemically reactive groups present on the baseplate structure are useful for chemoselectively ligating a COSM to the baseplate structure to create a polyoxime. For example, where the baseplate structure contains AOA groups and the COSM contains an aldehyde group such as glyoxylyl (GXL), oximation due to chemoselective ligation of the complementary orthogonal chemical groups results rapidly and essentially quantitatively in the formation of a homogenous preparation of a polyoxime of defined structure.

In embodiments of hetero-polyoximes where the baseplate contains potentially both aldehyde and amino-oxy chemically reactive groups, for example both AOA and GXL groups, one of the groups can be protected during chemoselective ligation of a first COSM having an orthogonal chemical reactive group complementary to the unprotected oxime-forming group on the baseplate. Protecting groups are shown in the Examples below. The second chemoselective ligation can then be performed following deprotection of the protected groups on the baseplate structure. Most easily, a first oxime bond (or set of bonds) can be formed prior to conversion of Ser to GXL, whereupon a second oxime bond (or set of bonds) can be formed through the newly formed GXL groups. The oxime bond is known to be stable during periodate oxidation of Ser to GXL. In this fashion very complex hetero-polyoximes can be formed. In a preferred embodiment a baseplate contains one or more lysines having an ε-AOA and one or more second lysines having an ε-Ser, wherein polyoxime synthesis occurs by a first oximation via the AOA group, followed by oxidation of Ser to GXL and a subsequent second oximation.

Alternatively, the baseplate can be conformationally designed to prevent intra-molecular oxime-formation, and furthermore the baseplate concentration and ratio of baseplate to COSMs can be set to minimize baseplate polymerization.

Hetero-polyoximes are also obtained by reacting a baseplate having uniform reactive groups to a mixture of COSMs (referred to as a COSM population).

In a further embodiment a baseplate can have at least one baseplate terminal residue attached to a reporter group or linker group, typically via a non-oxime linkage. The linker or reporter group can be ligated chemoselectively to the baseplate terminus or alternatively added during baseplate synthesis. A polyoxime containing an orthogonal linker group can be linked to a second polyoxime containing its complementary orthogonal linking group to yield a polyoxime dimer. Except for the complementarity of the linking groups, the polyoximes may be the same or different.

An individual COSMs is an organic molecule (which can contain an inorganic constituent) such as a peptide, a polypeptide, a lipid, an oligosaccharide, a nucleic acid sequence, or a combination of these molecular structures. Appropriately end-modified carborods are suitable COSMs. In an embodiment of the invention oxime formation occurs via aldehyde groups terminal to reducing sugars or created on sugars by mild chemical or enzymic oxidation. In another embodiment oxime formation occurs via an aldehyde group created by terminal oxidation of nucleic acid, such as exemplified by Reines and Cantor (Nucleic Acids Res. (1974) 1:767–786) for RNA, which is incorporated herein by reference, or created during chemical or enzymatic synthesis of a nucleic acid sequence. Such aldehydes are suitable complementary reactive groups to form oximes.

In one embodiment of homo-polyoximes of this invention, a COSM is a peptide. In another embodiment, a COSM and thus the polyoxime itself, is antigenic, preferably immunogenic. In one embodiment of hetero-polyoximes of this invention, at least one COSM is a peptide. In another hetero-polyoxime embodiment, at least one COSM of a polyoxime, and thus the polyoxime itself, is antigenic, preferably inmnunogenic. Antigenic polyoximes have utility in vitro and in vivo. In vitro, antigenic polyoximes are useful, for example, as reagents for immunoassays. In vivo, antigenic polyoximes serve as immunogens useful as vaccines, for example. In another embodiment of this invention, a polyoxime with an haptenic or antigenic peptide COSM provides an antigenic molecule having increased valency, compared to the peptide alone, and increased immunogenicity. Polyvalency generally leads to higher binding and to higher specificity of interaction, since more contacts are involved. In the case of a polyoxime comprising multiple copies of a ligand to a receptor, proximal receptors can be bridged if the COSM spacing and orientation provided by the baseplate is appropriate.

In view of the present disclosure, one skilled in the art can obtain a COSM having the appropriate complementary chemically reactive group. For example, a specifically active molecule such as a purified peptide COSM can be synthesized by SPPS. Following or during synthesis of the peptide, one of a pair of oxime-forming complementary orthogonal chemically reactive groups can be attached to the peptide using the methods described for the synthesis of baseplate structures. Other well-known methods also may be used to prepare polypeptide aldehydes, such as automated synthesis of peptide C-terminus aldehydes (see, for example, Murphy et al., *J. Amer. Chem. Soc.* (1992) 114:3156–3157, which is incorporated herein by reference). Oxime-forming complementary orthogonal chemically reactive groups can be attached in either a protected or an unprotected form. Methods to attach an oxime-forming complementary orthogonal chemically reactive group to a COSM include attachment through a chemically reactive side chain group. For example an oxime-forming complementary orthogonal chemically reactive group can be attached to a cysteine-containing COSM via the S atom by allcylation or disulfide formation. Then upon oximation to a baseplate the COSM is attached via its Cys residue through a thioether link (or disulfide bond) and an oxime link to the baseplate. Preferred alkylating compounds are alkyl halides having an attached AOA group. Preferred are Br—CH2—CO—NHCH2CH2NH—CO—CH2—O—NH—Boc, where the AOA group is protected and can be removed prior to an oximation step, and Br—CH2—CO—NHCH2CH2NH—CO—CH2—O—NH2. Another alkylating reagent is Br—$CH_2CH_2CH_2$NH—COCH$_2$ONH—Boc. The bromoacetyl group is much more reactive for alkylation of the thiol group of, for example, Cys residues. Less preferred is the iodoacetyl group because it sometimes is too reactive and may be lost by photolysis. Other alklylating groups, in addition to the bromoacetyl group, include the maleoyl group. As taught herein, linkers for protein modification using this group are exemplified as AOA-Lys(maleoyl-beta-alanyl)-OH and maleoyl -beta-alanyl-NHCH$_2$CH$_2$NH-COCH$_2$ONH$_2$. Although the maleoyl group is useful for making macromolecular conjugates, it is known to have serious stability problems (hydrolytic opening of the ring) and so is less suitable for making homogeneous polyoximes. Furthermore, alkylation involving the maleoyl group gives a linker which is more rigid and bulky than the link formed by alkylation with the bromoacetyl group, and is thus more visible to the immune system. A preferred linker for in vivo application is one against which an immune response is not directed. Examples of compounds for attachment of a oxime-forming complementary orthogonal chemically reactive groups to the side chain of cysteine through a disulfide bond are those containing a 2-pyridyl-S-S- radical. Preferred examples are 2-pyridyl-S-S-CH2CH2NH-CO-CH2O-NH-Boc and 2-pyridyl-S-S-CH2CH2NH-CO-CH2O-NH2. The resulting Cys-containing derivatives possess an aminooxy-acetyl (or protected aminooxyacetyl) group attached through a disulfide bond. The modification disclosed herein is useful for connecting COSMs to a polyaldehyde baseplate via a Cys side-chain through disulfide and oxime bonds. With this form of attachment, COSMs, e.g. peptides, can be liberated from the baseplate by disulfide reduction, a process which is known, to occur in the body. Such liberation of unmodified peptides can enhance an immune response against later presentation of the corresponding epitope on the natural pathogen. Polyoximes provide several advantages over small peptides (or non-peptides) imnmunogens, since the small molecules are typically not easily taken up by cells of the immune system and recognized as foreign without attachment to a carrier, e.g. a protein such as keyhole limpet hemocyaniin. The polyoxime baseplate or the polyoxime itself can provide an efficient, homogeneous presentation of the small molecule and can provide a source of "helper epitopes" to stimulate the immune system. By linking several copies of a small peptide together on a baseplate, a macromolecule is provided which is "seen" by the immune system and processed, including by degradation, for presentation and recognition by the immune system.

In additional embodiments of the invention, a heteropolyoxime contains both a binding peptide(s) for targeting (e.g. somatostatin analogs which bind to tumors over-expressing somatostatin receptors) and a cytotoxic peptide(s), such as ricin A-chain, that is released from the polyoxime construct after internalization by the target cell. This would mimic the process of the natural toxin where the ricin B-chain binds the cell, and subsequent to internalization of ricin and reduction of its S-S bonds the ricin A-chain is released into the cytoplasm resulting in cell death. When the A and B chains are linked by a non-breakable link, toxicity (effectiveness) is reduced by many orders of magnitude.

In additional embodiments polyoximes can be used in non-viral gene therapy delivery systems that require releasable elements.

The S—S bond provides a breakable link. Other breakable linkages include those that can be recognized by a specific hydrolytic enzyme(s) at a site of action or delivery, either in vitro or in vivo. Such hydrolytic enzyme sensitive linkages as are known in the art can be incorporated into the polyoxime as taught herein, and include but are not limited to restriction enzyme nucleotide sequences, lipid bonds recognized by a lipase, carbohydrate bonds recognized by a glycosidase, and peptide bonds recognized by a peptidase or protease. Breakable links, in addition to S—S links, can chosen for their preferential chemical sensitivity (over time if desired) to a particular chemical or physical environment (e.g. pH, temperature, presence of a catalyst, photolysis) occurring in vitro or in vivo, for example acid hydrolysis of a Asp-Gly peptide bond. In this way, release of active COSM can occur at a localized site without the requirement for cell internalization. Embodiments of the invention having releasable COSMs can be used for example in externally applied coatings or materials that change property in response to a change in environment, for example, a mildew preventative reagent that releases active anti-fungal ingredient in response to the presence of a fungal protein or enzyme (or a chemical change such as oxidation). Embodiments with non-releasable COSMs can be used for example in materials or coatings which are do not require release over time. For example, a waterproof suntan lotion can contain a hydrophobic template with UV-blocking COSMs attached in an active form.

Polyoxime embodiments of the invention can be used in improved kits for diagnostic purposes or as improved reagents for assays, for example, in binding assays such as immunoassays. For example, homogeneous polyoxime compositions bearing antigen peptides provide increased detection sensitivity in solid-phase immunoassays. The larger, multivalent polyoximes can more readily adhere to surfaces such as the multiwell plates used in immunoassays.

Also contemplated as embodiments of the invention are improved diagnostic kits containing polyoximes.

The aminooxyacetyl group and the dithiopyridyl group may be present on the same peptide COSM, for example as in $NH_2OCH_2CO$-Asp-Cys(S-2-pyridyl)-Thr-Leu-Ile-Asp-Ala-Leu-Leu-Gly-Asp-Pro-His-$NH_2$ (SEQ ID NO: 23). As determined herein, the presence of the 2-thiopyridyl protecting group on the Cys side chains does not prevent oxime formation. Such modified polyoximes have the added advantage that the 2-thiopyridyl group is useful for attaching yet further species (COSMs) as taught herein, via application of standard thiol chemistry (attack by a thiol to give a disulfide with loss of pyridine-thione, or reduction to a thiol followed by alkylation). In additional embodiments of the invention, applicable reactions for thiols with 2,2'dithiodipyridine (also known as 2,2'-dipyridyl disulfide) can be found in Brocklehurst and Little, *Biochem. J.,* (1972) 128:471–474. These reactions also apply to 4,4'-dipyridyl disulfide. For further embodiments of the invention, reactions with a 2-pyridylthio-derivatized thiol in protein chemistry are provided for example by Carlsson, J., Drevin, H. and Axen, R. (Biochem. J. (1978) 173:723–737). Other embodiments can contain sulfur protecting groups with similar chemical reactive properties as for those compounds described above. Additional embodiments include 2-thio-5-nitrobenzoic acid and 2-thio-5-nitropyridine. A preferred reagent is one that provides convenience of synthesis and product isolation, in addition to desired biological activity. Preferably a reagent which gives an easy separation between the desired derivative product and the reagent and by-products. Of course, selection of reagent also depends on the separation means employed and thus determination of the precise reagent is best left to the macromolecular chemist familiar with the particular lability and requirements of the macromolecule COSMs used. For example, DTNB introduces a negative charge, which can be exploited in ion exchange separations. For separation by reversed phase HPLC, reactions are performed on a small scale, including reagent blanks and a control reaction with cysteine. To examine results obtained overnight after automatic injection of such samples one selects for preparative scale applications the reagent giving the most convenient separation. A preferred reagent for general use and for use in initial studies is 2,2'-dithiodipyridine available commercially, e.g. from Fluka.

COSMs as taught herein which have an oxime-forming complementary orthogonal chemically reactive group and an additional reactive group, such as 2-thiopyridyl, that can react specifically with another non-baseplate macromolecule can themselves be used as linkers. For example, a COSM possessing both an AOA and 2-thiopyridyl functions can serve as a linker for attachment of another macromolecule or COSM through disulfide bond formation with the second macromolecule.

A COSM is further defined as consisting in part of a specifically active molecule or portion thereof. As used herein, the term "specifically active" indicates that the COSM has a defined biological, chemical or physical activity apart from its complementary orthogonal chemical reactivity. For example, a COSM may be specifically active as an antigen, an epitope or a hapten. Alternatively, a COSM may be specifically active as a receptor, such as a complementarily determining region of an antibody, or a ligand to a cell surface receptor.

The COSM alkylation described above provides another method of attachment of macromolecule such as antibody fragments to a baseplate. F(ab') fragments of IgG antibodies produced by reduction of the disulfide bonds which link the heavy chains of F(ab')2 fragments can be alkylated to contain an oxime forming complementary reactive group. In vivo the polyoxime will have reduced localization in the kidneys resulting in a reduced rate of excretion. The synthesis of compounds with multi-valent, hetero-specificities are now possible. For example, heteropolyoximes using different regions of the same IgG fragment or regions from IgGs with differing specificity can be made. Furthermore, antibody combining regions may be combined with receptor-binding, cell-binding or other ligand-binding molecules to create multi-valent antibodies. PCT/US88/03414 and Capon et al. (Nature (1989) 337:525–530; both are incorporated herein by reference), which exemplify "immunoadhesins," which are bispecific hybrid molecules that, for example, have a CD4 domain (to bind a gp120 protein of HIV) linked to a light chain or heavy chain constant region (Fc) of an IgG (to bind Fc receptors of phagocytic cells), provide some of the varying specificities that can be combined into a polyoxime of the invention.

As described herein for peptide baseplate structures, methods for regio-specific attachment or modification of C-termini via enzyme catalyzed reverse proteolysis or N-terminal serine or threonine residues (naturally present or engineered into the COSM) are applicable for COSM preparation. Natural or synthetic polypeptides carrying site-specifically placed aldehyde or amino-oxy groups also can be used as described, for example, by Offord, R. E., in *Protein Engineering: A Practical Approach,* pages 235–251, ed. Rees, et al. (Oxford Press, 1992), which is incorporated herein by reference. Reactive groups such as aldehydes can be placed site-specifically at the N-terminal of a recombinantly derived polypeptide (see for example Geoghegan et al. (*Bioconjugate Chem.* (1992) 3:138–146); Gaertner et al. (*Bioconjugate Chem.* (1992) 3:262–268). The combination of protein engineering by recombinant methods followed by site-specific modification to create COSMs capable of forming oxime linkages is a powerful tool for designing and creating homogeneous preparations of polyoximes of desired defined structure and activity. There is no limit on the size of the COSMs, as one merely prepares a baseplate in which the reactive groups are spaced further apart than in the present examples in order to accommodate larger polypeptide COSMs. Methods known in the art and as discussed herein for baseplate conformational design are applicable to COSM design as well.

A COSM also can be a specifically active chelator of metal ions or a molecule useful for binding a detectable marker. Such detectable markers include radionuclides, biotin, luciferin or a substrate for an enzymatic method of detection, such as 5-bromo-4-chloro-3-indolyl phosphate/nitro blue tetrazolium, which is a substrate for alkaline phosphatase (Sambrook et al., *Molecular Cloning: A Laboratory Manual* 2d ed. (Cold Spring Harbor Laboratory Press 1989), which is incorporated herein by reference). Suitable metal chelating molecules include, but are not limited to, chelates of EDTA (ethylenediamine-tetraacetic acid) and analogs of EDTA as described in U.S. Pat. No. 4,678,667, which is incorporated herein by reference. Such analogs are capable of complexing with metal ions including radioactive metal ions as described in U.S. Pat. No. 4,622,420, which is incorporated by reference herein. COSMs may also consist of other chelators such as AOA-desferrioxamine, which chelates, for example, gallium-67 and gallium-68, or AOA-biocytin, which contains biotin in soluble form.

Where the metal ion is radioactive, such polyoximes are particularly useful in vivo for imaging or treating malignant tissues or a tumor. Using the present disclosure and available public knowledge, one of skill in the art would know how to construct baseplates containing these COSMs for in vitro diagnosis and in vivo diagnosis and treatment. For a description of general methodology, see, for example, U.S. Pat. Nos. 5,185,143, 5,011,676, 5,087,616, 4,707,352, 5,084,266, 4,918,164, 4,865,835, 4,861,581, 4,659,839, 4,652,440, and 4,444,744, which are incorporated herein by reference.

As noted above, parallel assembly of polyoximes by chemoselective ligation is the result of the complementary orthogonal chemical reaction between, for example, a GXL group on the baseplate structure and an AOA group on the COSM to form a homogeneous preparation of a polyoxime having a defined macromolecular structure. Other embodiments of polyoximes have the reverse complementary structures, i.e. amino-oxy baseplate and aldehydic second organic molecule, from those described above. These are particularly indicated when a series of aldehyde-containing molecules is available (e.g. sugars). However, generally preferred embodiments contain aldehyde baseplates.

The invention also provides methods of parallel assembly to create polyoximes, either homo- or hetero-polyoximes. As described above, chemoselective ligation results in the formation of polyoxime molecules having defined structure and characteristics. Example 3 demonstrates unexpected and surprising features of polyoxime formation by parallel assembly with baseplates of valency greater than two, including: ease, rapidity, and mildness of synthesis; essentially quantitative yield; and apparent lack of steric hindrance. Example 14 demonstrates the formation of hetero-polyoximes.

Other functional groups including biologic entities, but not limited to a reporter group (such as biotin or a chelator for a radiometal), a lipophilic anchor (such as tripalmitoyl-S-glycerol-Cys) or an orthogonal reactive linking group (such as bromoacetyl or a masked thiol such as S-acetylthioacetyl or S-S-2-pyridyl) can be added to the baseplate prior to oximation. Baseplates containing biocytin or N-acetyl-cysteine are provided in examples by way of illustration. The modified baseplates allow additional flexibility in using the polyoximes, such as for vaccines or biosensors. Reporter-tagged embodiments of polyoximes of the invention are monitored via the reporter group. Stable polyoximes possessing both a lipophilic anchor and a defined molecular structure are useful, for example, for insertion of the polyoxime into membranes, which can enhance vaccine production, or into other lipophilic environments. Attachment of the polyoximes to other macromolecules, to each other, or to surfaces is furthered by embodiments having a different non-oxime orthogonal reactive linking group for use in forming the desired linkage.

The di- and trivalent baseplates described in the following Examples section preserve symmetry. However, polyoximes with positional isomers can be formed, for example by using as a baseplate H-Gly$_3$-Lys(COCHO)-Lys(COCHO)-Gly-OH (SEQ ID NO: 11); in such cases the environment of the first lysine is not identical to that of the second one. More generally, the baseplate can be deliberately synthesized to favor interaction with a target structure and have no symmetry.

Additional hetero-polyoxime embodiments of the invention are made by hetero-polyoxime formation using a baseplate having four reactive groups in which three reactive groups of one orientation are unblocked and reacted with peptide COSM, which is then followed by deprotection of the fourth baseplate reactive group and reaction with a different COSM.

Additional hetero-polyoxime embodiments of the invention are COSM libraries. A preferred library is made from peptide COSMs. Polyoxime peptide libraries can be prepared from a baseplate and a mixture of peptide COSMs (COSM population). The peptide portion of each COSMs can be designed following known methods for designing standard linear peptide libraries. For example, Jung et al. (in Solid Phase Synthesis, R. Epton, Ed. 1992, Interceptor, Andover, UK, pp 222–235) provides a brief review of design, synthesis and methods of use of standard synthetic linear peptide libraries. Peptide sequences to be represented in a polyoxime peptide library are synthesized to contain a reactive chemical group complementary to at least one oxime-forming chemically reactive group on a baseplate. Peptide sequences can be synthesized individually or in mixtures. The peptide COSMs or mixtures can be reacted individually or in combination with a baseplate to form a polyoxime library. The peptide COSMs can also be reacted sequentially with a baseplate to form defined hetero-polyoxime compounds. Intermediate polyoximes formed during polyoxime formation can be isolated. Intermediate polyoximes contain unreacted oxime-forming groups. The intermediate polyoximes can then be reacted with another individual peptide COSM or peptide COSM mixture to prepare more complex hetero-polyoxime libraries. If necessary or desired, excess amino-oxy compounds (or aldehydes) may be removed for example by passage down an aldehyde (or amino-oxyacetyl) gel column, respectively, prior to screening (as described below) or other use. The polyoxime libraries can be used in iterative screening processes in a fashion similar to those for standard peptide libraries.

Appropriately chosen baseplates can act as "the palm of a hand" with the peptide "fingers" ready to close around or interact with a target structure. In various embodiments the "palm" baseplate is varied, to optimize spacing, bydrophilicity, charge, etc.

By way of illustration, if we consider a library of just the 400 dipeptide amides formed from 20 common L-amino acids, all carrying the arninooxyacetyl group, and a polyaldehyde baseplate of valency 3, then neglecting symmetry considerations the number of possible trioximes obtained on mixing should be $400^3 = 6.4 \times 10^7$.

Numerous strategies have been developed for the screening of synthetic peptide libraries. In using polyoxime peptide libraries the strategy for optimization is essentially as described by Houghten et al. (Nature (1991) 354:84) and Geysen and Mason (Bio. Med. Chemistry Lett. (1993) 3:397404), except that there the authors use linear peptides only. For example, 400 sets of peptides can be made, one starting with Gly-Gly-Xaa-Xaa-Xaa-Xaa (SEQ ID NO: 14), the next Gly-Ala-Xaa-Xaa-Xaa-Xaa (SEQ ID NO: 15), etc. so as to have all 20 coded amino acids in position 1 and all in position 2. The Xaa-Xaa-Xaa-Xaa refers to the four succeeding positions where all amino acid residues are present at all positions. Screening the 400 samples with appropriate assay can identify at least one as most active. For example, if an Arg-Tyr-Xaa-Xaa-Xaa-Xaa (SEQ ID NO: 16) sequence was found to be most active, then in a next screening round, Arg-Tyr is fixed for the next 400 samples to yield Arg-Tyr-Gly-Gly-Xaa-Xaa (SEQ ID NO: 17), Arg-Tyr-Gly-Ala-Xaa-Xaa (SEQ ID NO: 18), etc. If after screening, Arg-Tyr-Lys-Glu-Xaa-Xaa (SEQ ID NO: 19) was found as most active, then a final screen involving 400 more samples, all starting with Arg-Tyr-Lys-Glu and having either Gly-Gly, Gly-Ala, etc. at the C-terminus is undertaken. A similar approach is used for polyoxime libraries except that, instead of using linear hexapeptides for assay, these peptides are mounted on a baseplate via parallel-assembly and oxime bond formation.

The advantages of using polyoxime libraries include: 1) the baseplate can contain a structure which is active in an assay, thus permitting the use of lower concentrations of polyoximes in an assay and so minimize solubility problems, which can otherwise be quite severe; and 2) polyvalency generally leads to higher binding and to higher specificity of interaction, since more contacts are involved.

Baseplates preferably contain aldehyde chemically reactive groups; however, other embodiments of polyoxime peptide libraries having the reverse complementary structures, i.e. amino-oxy baseplates, are particularly indicated when a series of aldehyde-containing molecules is available (e.g. sugars).

In some polyoxime library embodiments, a part of the polyoxime structure can be synthesized by conventional methods and oximation is used to add additional elements that represent the sequences of interest in a library. By way of illustration, the examples provided herein demonstrate attachment of non-identical peptide COSMs to a baseplate.

The use of aminooxyacetyl- (or aldehyde-modified-) monomethoxy-polyethyleneglycol, or other homologous series of polymers as COSM mixture, allows a polyoxime to have heterogeniety within the molecule itself. Such polyoximes are formed by parallel assembly of a mixture of members of a homologous series, such as: $NH_2OCH_2CO-NH-CH_2CH_2O(CH_2CH_2O)_nCH_2CH_2OCH_3$ or $O-CHCH_2O(CH_2CH_2-O)_nCH_2CH_2OCH_3$ or $O=CHCONHCH_2CH-O(CH_2CH_2O)_nCH_2CH_2OCH_3$, where n is an integer. Aldehydic- and AOA-modified molecuies of a homologous series can be used in parallel assembly polyoxime formation. In the context of protein modification, COSM embodiments of the invention allow protein PEGylation that can increase stability, solubility, and half-life. Alternatively, several chains can be attached to a baseplate which is itself attached to a protein. Although the products are then slightly not homogenous because of integer n taking a series of values, the polyoximes can be useful, for example, for prolonging the biological half-life of small proteins or reducing the immunogenicity of therapeutic proteins.

In a separate embodiment, the polyoxime is further characterized as having the ability to induce an immune response in an animal. Immunogenic polyoximes that are formed from a baseplate structure covalently bonded to a plurality of a COSM with immunogenic properties have the ability to induce an immune response in the animal. For the purposes of illustration only, such a COSM can be a peptide or a polypeptide corresponding to a hapten, a cell surface receptor or fragment thereof, a metal chelating agent or the epitope of a viral antigen. Many different immunomodulating peptide COSMs exist, such as the peptides described by Hobbs et al. (*J. Immunol.* 138:2581–2586 (1987)), Antoni et al. (*J. Immunol.* 137:3201–3204 (1986)) and Nencioni et al. (*J. Immunol.* 139: 800–804 (1987)), which are incorporated herein by reference.

Various peptides attached to chelating agents also are well known and include, for example, the melanocyte stimulating hormone peptide derivatives (Eur. Pat. Appl. 0 498 771 A2, filed Mar. 2, 1992, which is incorporated herein by reference). These polyoximes are useful in vivo as vaccines and imaging agents.

In another embodiment, COSMs can be nucleic acid sequences, which can be chemoselectively ligated to a baseplate. Also, nucleobases can be coupled to peptide or polypeptide sequences to create a polypeptide-nucleic acid (PNA), which can be used as a COSM and ligated to a baseplate. When used in conjunction with detectable markers, such as $^{32}P$, biotin, radiolabelled chelators, or enzymes such as alkaline phosphatase (or a substrate thereof), the resulting polyoximes provide highly specific and reactive nucleic acid probes which are useful in various diagnostic techniques, for example, northern and Southern hybridization assays (see Sambrook et al. (1989)).

In a separate embodiment, the polyoxime has a plurality of a COSM which is a polypeptide having a sequence identical to the sequence of a complementarity determining region (CDR) of an antibody. As is known to one of skill in the art, the CDR may be coupled to a metal chelating agent to create a bifunctional COSM, or alternatively, the chelating or reporter agent is coupled to the baseplate as described herein. CDR polyoximes are useful in vitro and in vivo. In vitro, they can used in a place of polyclonal and monoclonal antibodies in various immunoassays. In vivo, they are useful to passively immunize an animal or to diagnose and treat a disease.

Polyoximes of the present invention are also useful in purifying biologically active molecules of interest that can bind to a polyoxime (for general methodology see for example Sambrook et al. (1989) and Harlow and Lane (1988)).

Polyoximes can be attached to a solid phase, such as the surface of a silicon chip, a tissue culture plate, or a synthetic or natural resin. One can chemoselectively ligate a polyoxime to a solid phase through the use, for example, of thiol groups temporarily protected with thiopyridyl or acetyl groups to form a thioether or a thioester bond. Alternatively, polyoximes can be attached to a solid phase, such as a lipid layer or cell membrane, via lipid anchor groups covalently attached to the baseplate portion of a polyoxime. COSMs of polyoximes adhered or attached to solid surfaces can be used as ligands for purification of or detection of the presence of a target molecule that binds the COSM ligand. If the COSM is attached to the baseplate via a breakable link, such as one containing an S—S bond as taught herein, a COSM-target pair can be released from the baseplate/surface to facilitate purification of analysis.

A soluble complex for targeting a biologically active module to a cell also is provided by this invention. The soluble complex is comprised of a baseplate structure ligated to a plurality of a biologically active molecule and linked to a cell specific binding agent. Alternatively, the baseplate can be ligated to a plurality of a cell specific binding agent and linked to a biologically active molecule. Such soluble complexes provide cell or tissue specific delivery systems to the cell expressing the appropriate receptor. Biologically active molecules include, but are not limited to, homogeneous antibody CDR, antibody fragments, epitopes, paratopes, nucleic acids, ligands specifically reactive with cellular receptors, and cellular receptors or fragments thereof that retain the ability to specifically bind their target molecule. The biologically active molecule also can be a peptide having attached thereto a therapeutic agent, for example, a toxin, chemotherapeutic agent or radioisotope. For the purposes of this invention, a cell specific binding agent is a molecule that recognizes and binds specific biological molecules. Such agents include but are not limited to antibodies, antibody fragments, and cell surface receptors (or biologically active fragments thereof). For example, the cell specific binding agent can be a tumor cell-specific receptor, a cell surface receptor, or a ligand for a cell surface receptor.

In addition to compositions containing only polyoximes, also within the scope of this invention are compositions containing polyoximes of the invention and at least one other ingredient. Also embodied are pharmaceutical compositions comprising a therapeutic polyoxime embodiment of the invention and a pharmaceutically acceptable carrier.

Also provided by this invention is a method of inducing an immune response in an animal which comprises administering to the animal an immunogenically effective amount of an antigenic polyoxime, defined above, in a pharmaceutically acceptable carrier. For the purposes of this invention, an animal is preferably a vertebrate, such as a mammal, especially a murine, simian or human. In one embodiment, the animal is a human patient. Depending on the antigenic polyoxime, the immune response that is induced is humoral or cellular immunity, or both.

The polyoximes of the invention have several novel characteristics. One novel haracteristic for synthetic homo-polyoxime molecules of this invention is that the polyoximes preparations are homogeneous. Polyoximes are multivalent, are stable in aqueous solution or semi-aqueous solution, and can be prepared at temperatures from −3° C. to 50° C., but most advantageously at room temperature. The polyoximes of this invention have utilities related to the specific biological reactivity and specific chemical and physical reactivities of their individual component parts.

As demonstrated herein, the complementary reactive groups that interact to form an oxime linkage between baseplate and COSM are highly specific. The oximation reactions taught herein provided complete or essentially quantitative yield of the reaction product. Such complex molecule formation occurs under very mild conditions. Rapidity is particularly surprising under dilute conditions which are often useful to minimize inter-molecular aggregation or reactions. The oximation reaction can occur unattended, such that self-assembly of the polyoximes takes place. Polyoximes are easily purified by virtue of the essentially quantitative yield and because trace intermediates and the final product typically differ substantially (i.e., by the presence or absence of at least one COSM unit) so that methods for their separation are readily chosen and applied. Oxime linkages have superior hydrolytic stability over a range of physiological conditions compared to hydrazones or the like. Oxime linkages are not commonly subject to enzymatic hydrolysis. Thus polyoximes have the advantage of being particularly suited to applications where integrity and stability of a complex is desirable. As demonstrated in the examples, the polyoximation reaction is very mild and thus is suitably advantageous for preparing biological macromolecules retaining biological activity or function. The polyoxime chemistry dispenses with the need to have reversible chemical protection of subunits. A great flexibility is provided herein for site-specific modification of both baseplates and COSMs to create reactive groups capable of forming oxime linkages. Because of this flexibility and the absence of the need for reversible protection, the design of baseplates and COSMs extends to both artificial and natural molecules and their derivatives. The surprising lack of steric hindrance demonstrated herein (e.g. a 23-mer peptide attached to each of the side-chains of seven consecutive lysine residues) indicates that complex molecules can now be designed. In such complex molecules the individual capabilities of the subunits can be enhanced and combined, the whole being greater than the sum of the parts. For example, baseplates can be designed to improve solubility of peptides as well as present peptides to receptors or antibodies or the immune system of an animal in multi-valent and/or constrained forms. Polyoximes formed from synthetic baseplates and COSMs have the additional advantage of being virus free.

The following examples are provided by way of illustration and not by way of limitation of aspects of the present invention.

EXAMPLES

Example 1

Synthesis Of Peptide Baseplate Structures Having Chemically Reactive Aldehyde Or Amino-oxyacetyl Groups.

Synthesis of GXL-baseplate structures:

Peptide baseplate structures were constructed using solid phase peptide synthesis (SPPS). Briefly, automated SPPS was performed using a model 430A peptide synthesizer (Applied Biosystems, Inc.). The desired amino acid sequence was programmed into the synthesizer and synthesis proceeded using the standard Fmoc protocol. The starting resin was Gly-PAM polystyrene (0.5 mmol per synthesis). Two different peptide sequences were synthesized:

H-Gly$_3$-[Lys(Boc)]$_5$-Gly-PAM resin and H-Gly$_3$-[Lys(Boc)]$_7$-Gly-PAM resin.

The Boc groups were removed using trifluoroacetic acid (SFA). Briefly, about 15 ml of TFA was incubated with one gram of resin for one hour at room temperature. The sample was then filtered, washed with dichloromethane and dried. The free (x- and e-amino groups were acylated using two equivalents of active Boc-Ser (benzyl) N-hydroxysuccinimide ester (0.16 M in dry DMSO) over each amino group. The apparent pH was measured using water-moistened pH paper and was adjusted to pH 8–9 with N-methylmorpholine. The resin was the agitated for two hours. Following this reaction, the standard ninhydrin test showed that acylation was incomplete. Thus, the resin was filtered and the acylation reaction was repeated, maintaining the apparent pH 8–9 with N-methylmorpholine. Following this reaction, the ninhydrin test showed that acylation was essentially complete. The resin was filtered, washed with DMSO, then with dichloromethane and dried under vacuum. The reaction yielded 1.7 g resin from 1.3 g H-Gly$_3$-[Lys(Boc)]$_5$-Gly-PAM resin.

Cleavage-deprotection was achieved by dissolving the sample in 17 ml TFA. The mixture was stirred for 30 min, then 1.7 ml trifluoromethane sulfonic acid (TFMSA) was added. The solution was agitated for one hour and peptide was precipitated using dry ether.

The peptide was washed three times with dry ether and dried under vacuum. The resulting mixture of peptide and cleaved resin was resuspended in 60 ml water. The peptide, which is soluble in the water, was dissolved and the solution was filtered.

Following lyophilization, the filtrate was dissolved in 50 ml water and purified in 5 ml portions by RP-HPLC (Waters) on a 250×21 mm id NUCLEOSIL 300A 5 $\mu$m C8 column run at 10 ml/min. Solvent A was 0.1 I% TFA and solvent B was 0.1% TFA in 90% acetonitrile. The peptide was purified isocratically at 100% A and eluted soon after the front. The column was then washed with 50% B and equilibrated with 100% A prior to the next injection. The product, H-Ser-Gly$_3$-[Lys(H-Ser)]$_5$-Gly-OH (SEQ ID NO: 7) (yield=100 mg) eluted as a single peak by analytical RP-HPLC (250×4 mm id column; packing and solvents as above) at 0.6 ml/min isocratic 100% A for 5 min, followed by a linear gradient of 2% per min B to 100% B. The retention time of the peptide was 20 min.

The purified peptide was characterized by electrospray ionization mass spectrometry (ESI-MS). A Trio 2000 spectrometer fitted with a 3000 amu rf generator was used (Fisons Instruments; Altrincham, UK). Samples were infused at 2 $\mu$l/min in water/methanol/acetic acid (49.5/49.5/1 by vol). The measured molecular weight of the sample was determined as 1410.12+/–0.66 daltons compared to the calculated expected value of 1409.56 daltons.

The serine groups on the precursor baseplate structure were converted into chemically reactive glyoxylyl (GXL) groups by mixing 0.2 ml H-Ser-Gly$_3$-[Lys(H-Ser)]$_5$-Gly-OH (SEQ ID NO: 7) (10 mM in water) with 7.8 ml imidazole-HCl buffer, pH 6.95, and adding 0.24 ml NaIO$_4$ (0.1 M in water). The mixture was rapidly mixed, then incubated at room temperature for 5 min. The oxidation reaction was terminated by adding 0.48 ml ethylene glycol (0.1 M in water) and rapid mixing the solution. The same was adjusted to pH 4.0 with acetic acid and the solution was injected onto a RP-HPLC 250×10 mm id Nucleosil 300A 7 $\mu$m C8 column. Elution was at 4 ml/min using isocratic 100% A for 5 min, followed by a linear gradient of 2% B/min to a final concentration of 100% B. The hexa-GXL-baseplate (SEQ ID NO: 6) eluted at retention time of 16 min.

Solvent was removed by vacuum centrifugation (Speed-Vac; Savant Instruments) without heating. The reaction yielded approximately 1 mg of purified hexa-GXL-baseplate, which was stored as a powder at –20° C. and was stable for at least several weeks. Similar methods were used to prepare octa-GXL-baseplate (SEQ ID NO: 9).

Synthesis of AOA-baseplate structures:

Alternatively, the amino groups in the baseplate peptide were converted to AOA groups to create poly-AOA-baseplate structures. Briefly, H-Gly$_3$-Lys$_5$-Gly-PAM resin was incubated with Boc-AOA N-hydroxysuccinimide ester (0.1 M in dry DMSO; 2.5 equivalents over each amino group; 50 ml per 0.69 g resin, apparent pH 8–9 with N-methylmorpholine). The acylation reaction was complete after two hours incubation at room temperature, as shown by the standard ninhydrin test.

The resin was filtered, washed with DMSO, then dichloromethane and dried under vacuum. Cleavage-deprotection was achieved using a solution containing 7 ml TFA and 0.7 ml TFMSA. The sample was precipitated with ether, then dissolved in water, filtered and lyophilized as described above.

The lyophilized crude product was dissolved in 4 ml water and 0.5 ml fraction were purified by RP-HPLC using the above-described 21 mm column operated at 10 ml/min. After 5 min elution at 100% A, a gradient of 1% B/min was applied to a final concentration of 5% B, which was maintained for 20 min. The column was washed with 50% B and equilibrated with 100% A prior to each injection.

The hexa-AOA-baseplate product (SEQ ID NO: 5) eluted during the isocratic elution at 5% B. The product eluted as a single peak on analytical RP-HPLC. The mass was determined by ESI-MS to be 1325.49+/–0.38 daltons as compared to the calculated mass of 1325.4 daltons. Following removal of the solvent, the hexa-AOA-baseplate was stored as a powder at –20° C. and was stable for at least several weeks. The storage vial was kept tightly sealed and volatile aldehydes were excluded.

Example 2

Synthesis Of Peptide Complementary Orthogonal Specifically Active Molecules (COSMs).

The peptide component of COSMs was synthesized using the SPPS method described above. A twelve amino acid peptide having the sequence Lys-Leu-Glu-Glu-Gln-Arg-Pro-Glu-Arg-Val-Lys-Gly (SEQ ID NO: 1), which corresponds to amino acid residues 102 to 112 of human translationally controlled tumor protein (TCTP) containing an addition C-terminus glycine was synthesized. Automated peptide synthesis was performed using a model 430A peptide synthesizer (Applied Biosystems, Inc.) as described in Example 1, except that a Sasrin resin (Bachem) was used and Pmc was used as side-chain protection for arginine residue.

The $\alpha$-amino group of the lysine residue at the N-terminus of the TCTP peptide was converted to an $\alpha$-AOA group by incubating 0.33 mmol TCTP-resin with Boc-AOA N-hydroxysuccinimide ester as described in Example 1. Cleavage-deprotection was performed using 1.5 ml of a mixture of phenol/ethanedithiol/thioanisole1 water/TFA (0.75 g/0.25 ml/0.5 ml/0,5 ml/10 ml). Following stirring for three hours, the mixture was filtered and the peptide was precipitated with 4 ml cold methyl-tert-butyl ether. The precipitate was washed three times with the same ether and dried.

The dried precipitates were dissolved in 15 ml water and purified in 1.5 ml portions by RP-HPLC on the 21 mm id column described in Example 1. The column was eluted at 10 ml/min with 100% A for 5 min, then 1% B/min to a final concentration of 9% B, which was maintained until the product eluted (retention time approximately 45 min). The column was 30 washed with 50% B and equilibrated with 100% A prior to each injection.

Following solvent removal by vacuum centrifugation, the AOA-TCTP sample (SEQ ID NO: 4) was characterized by ESI-MS. The molecular weight of the sample was determined to be 1542.57+/−1.14 daltons, as compared to the expected value of 1541.73 daltons. The reaction yielded 120 mg AOA-TCTP from 1.3 g. AOA-polypeptidyl resin. The AOA-TCTP COSM was stored as a powder at −20° C. and was stable for at least several months.

Alternatively, an N-terminal serine residue was added to 707 mg (0.17 mmol) of the TCTP-Sasrin resin on the Applied Biosystems 430A peptide synthesizer. Following removal of the Fmoc group, cleavage-deprotection was performed as described for the AOA-TCTP COSM. The Ser-TCTP precursor COSM (SEQ ID NO: 2) was purified by RP-HPLC (yield 90 mg) and characterized by ESI-MS. The molecular weight of the Ser-TCTP precursor COSM was determined to be 1556. 53+/−1.07 daltons as compared to the expected value of 1555.75 daltons. The Ser-TCTP precursor COSM was stored as a powder at −20° C. and is stable indefinitely.

The precursor was converted to the chemically reactive GXL-TCTP (SEQ ID NO: 3) by adding 1.2 ml precursor Ser-TCTP COSM (10 mM in water) to a solution containing 6.8 ml imidazole-HCl buffer (50 mM, pH 6.95) and 0.24 ml $NaIO_4$ (0.1 M in water) and rapidly mixing the sample. After 5 min at room temperature, the oxidation reaction was stopped by addition of 0.48 ml ethylene glycol (0.1 M in water). The solution was adjusted to pH 4.0 with acetic acid and the GXL-TCTP was isolated by RP-HPLC on the 10 mm id column. Elution was performed at 4 ml/min with 100% A for 5 min followed by 2% B/min to 100% B. The retention time was 19 min.

After solvent removal, the GXL-TCTP was characterized by ESI-MS. The molecular mass of the sample was determined to be 1524.63+/−0.16 as compared to the expected value of 1524.70. The GXL-TCTP COSM was stored as a powder at −20° C. and was stable for at least several weeks.

A twenty-three amino acid peptide corresponding to residues 43 to 65 of the human proinsulin C peptide sequence (Pep C) also was synthesized on the Applied Biosystems 430A peptide synthesizer using the standard Fmoc protocol. Fmoc-Arg (Pmc)-Sasrin resin (Bachem) was used at a 0.5 mmol scale. While still protected as a resin-bound peptide, 100 mg resin (approximately 20 umol of the N-terminus (Y-amino group) was acylated using Boc-AOA N-hydroxysuccinimide ester as described above.

Following cleavage and deprotection using 3.5 ml of the phenol mixture described above, the AOA-Pep C COSM (SEQ ID NO: 10) was purified by RP-HPLC (yield=8 mg). The molecular mass of the AOA-Pep C COSM was determined by ESI-MS to be 2308.56+/−0.11 daltons as compared to the calculated value of 2308.576 daltons. The AOA-Pep C COSM was stored as described above and was stable for at least several months.

Example 3
Parallel Assembly Of Hexa-TCTP-Polyoximes By Chemoselective Ligation Of A Hexa-GXL-baseplate And AOA-TCTP COSMS.

Parallel assembly of the hexa-TCTP-polyoxime was initiated by adding 200 μl AOA-TCTP (SEQ ID NO: 4) (10 mM in 0.1 M sodium acetate buffer, pH 4.6) to 6.7 μl hexa-GXL-baseplate structure (SEQ ID NO: 6) (10 mM in water). After mixing, the oximation reaction was allowed to proceed at room temperature. AOA-TCTP (2 μmol) was present in about a five-fold molar excess over baseplate (67 nmol; about 400 nmol GXL groups). The structure of the predicted hexa-TCTP-polyoxime product is shown in FIG. 1.

Figure 3:
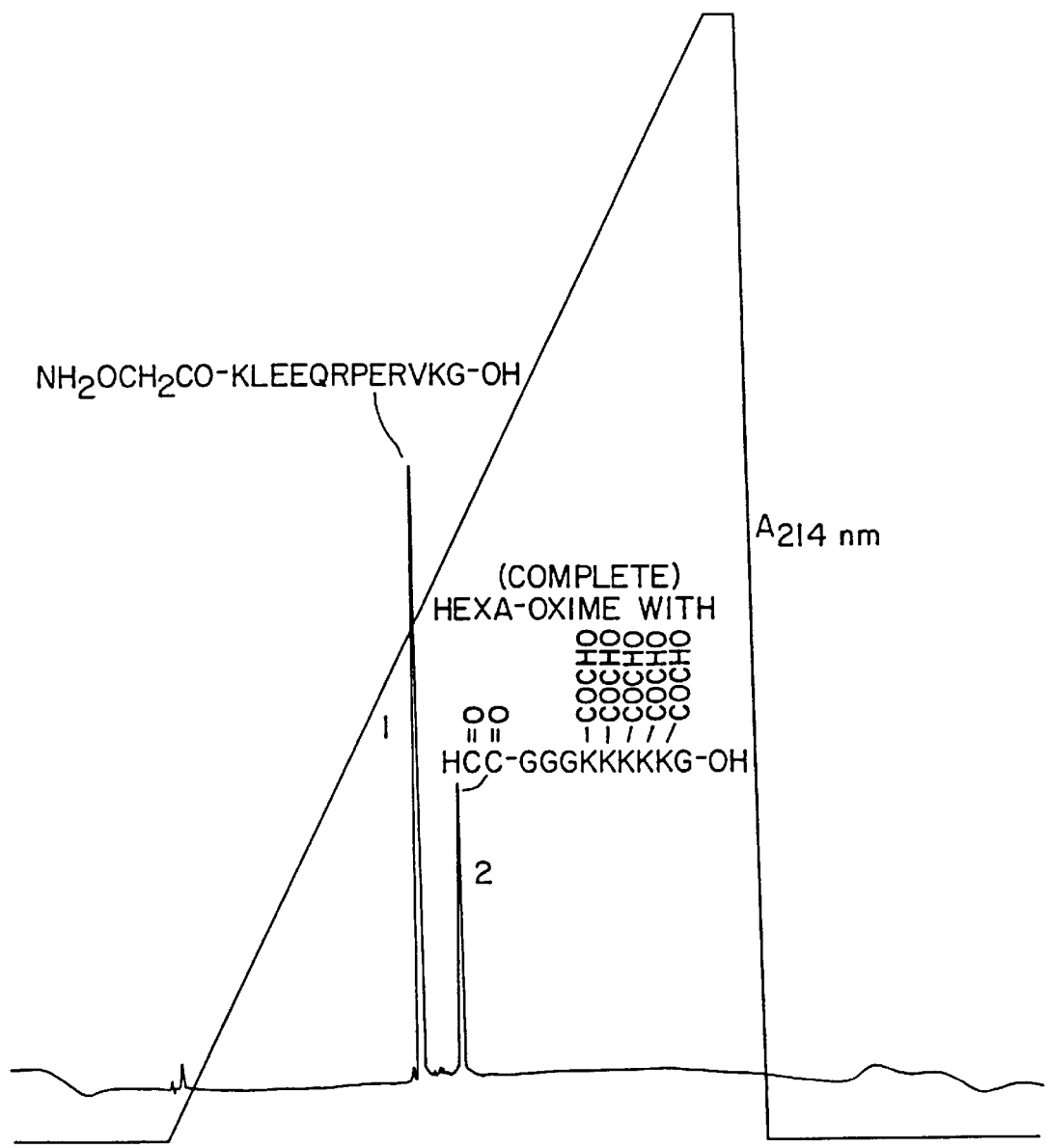
FIG. 3 shows the chromatogram obtained during RP-HPLC of a sample 18 hours after beginning the oximation reaction. Peak 1 indicates the fraction containing unbound TCTP-COSM, and Peak 2 indicates the fraction containing hexa-TCTP-polyoxime product.

The extent of chemoselective ligation was monitored by measuring the formation of the hexa-TCTP-polyoxime by RP-HPLC using the 4 mm id column. Elution was at 0.6 ml/min with 100% A for 5 min, followed by a gradient of 2% B/min from 0 to 100% B. Elution of the sample was monitored by absorption at 214 nanometers. Chromatograms obtained after 3 hours (FIG. 2) and after 18 hours of incubation (FIG. 3) are shown. After 3.5 hours of incubation the polyoxime peak, when analyzed on a shallower gradient, displayed a mixture of tri-, tetra-, penta- and hexa-oxime forms (data not shown). Formation of the hexa-TCTP-polyoxime was essentially complete after 18 hours of incubation.

The reaction was terminated and hexa-TCTP-polyoxime product was purified by preparative RP-HPLC. Preparative scale reaction mixtures were purified in 0.5 ml portions on a 250×20 mm id column packed with NUCLEOSIL 300A 5 um C8. Elution was performed at 4 ml/min with 100% A for 5 min, followed by a linear gradient of 1% B/min to a final concentration of 100% B.

Excess AOA-TCTP eluted at a retention time of 44 min and hexa-TCTP-polyoxime product eluted at 50 min. Both the hexa-TCTP-polyoxime product and the excess of AOA-TCTP were recovered during purification. After vacuum desiccation, yield was calculated as 11 mg of hexa-TCTP-polyoxime obtained from 45 mg AOA-TCTP and 1.4 mg hexa-GXL-baseplate.

The hexa-TCTP-polyoxime was characterized by polyacrylamide gel electrophoresis in the presence of sodium dodecyl sulfate (SDS-PAGE) using the PHAST electrophoresis system (Pharmacia).

Protein samples were applied to a 20% gel and electrophoresis was performed at 15° C. for 90 volt-hours and visualized by silver stain. Protein molecular weight standards (Pharmacia) were run in parallel lanes and included phosphorylase-B (94 kDa), bovine serum albumin (67 kDa), ovalbumin (43 kDa), carbonic anhydrase (30 kDa), soybean trypsin inhibitor (20.1 kDa) and α-lactalbumin (14.4 kDa), as indicated in FIG. 4.

Figure 4:
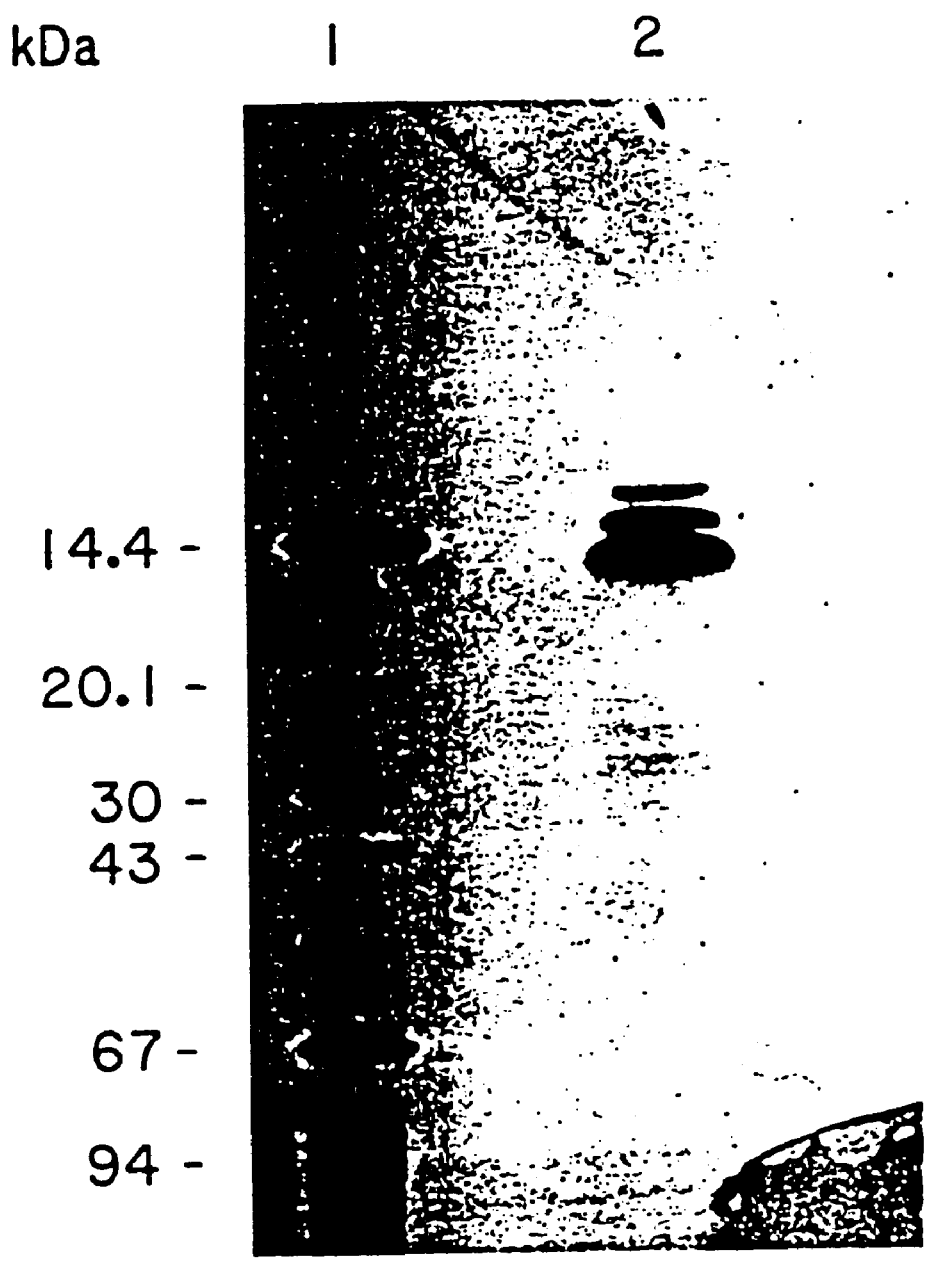
FIG. 4 is a photograph of a polyacrylamide gel showing the migration of the hexa-TCTP-polyoxime. Lane 1, protein standards. Lane 2, hexa-TCTP-polyoxime.

As shown in FIG. 4, the hexa-TCTP-polyoxime product migrated as a major band having an apparent molecular weight of about 14 kDa, which is greater than the predicted molecular weight of about 10 kilodaltons (kDa). The greater molecular weight is likely due to the expected extended structure of the hexa-TCTP-polyoxime. The presence of faint bands having faster mobility in the sample lane are likely due to partial decomposition of the sample due to boiling the sample prior to gel loading. The stability of the hexa-TCTP-polyoxime is discussed below.

Figure 5:
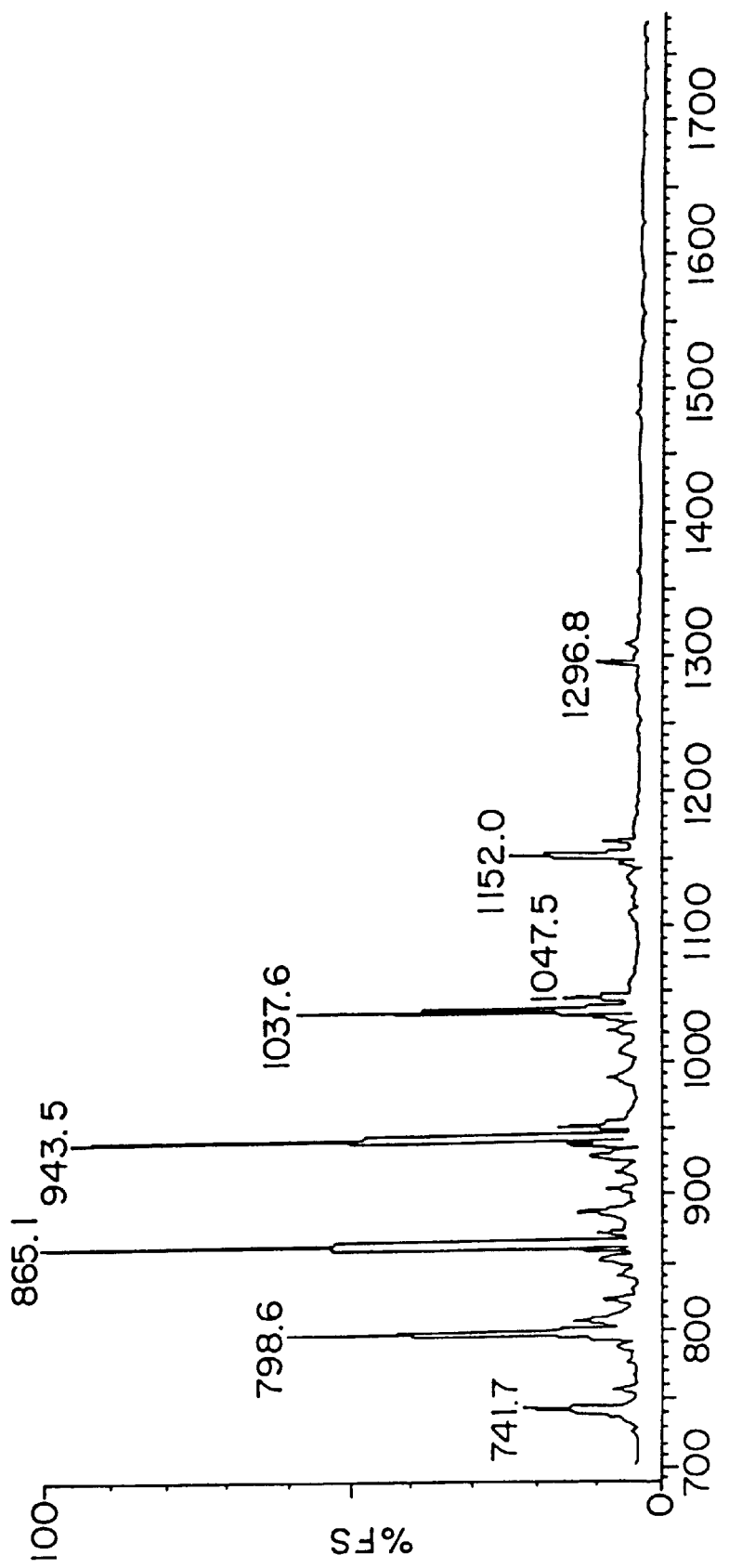
FIG. 5 shows a mass spectrum obtained by electrospray ionization mass spectrometry of the hexa-TCTP-polyoxime. Vertical axis indicates the percent full scale of detector response (% FS); horizontal axis indicates mass-to-charge ratio (M/Z). The numbers on the peaks indicate the M/Z value of each high molecular weight species that carries several positive charges (protons). For example, the peak at M/Z=1037.6 carries 10 protons (Z=10). The mass (M) of the corresponding species can be calculated as (10)×(1037.6)= 10376, minus 10 (for the ten protons)=10366 amu. The average mass calculated from all the signals is 10367.41±1.28. The theoretical value is 10365.49. A Trio 2/3000 ESI data system was used (found 10367.41±1.28 , calc. 10365.49).
Figure 6:
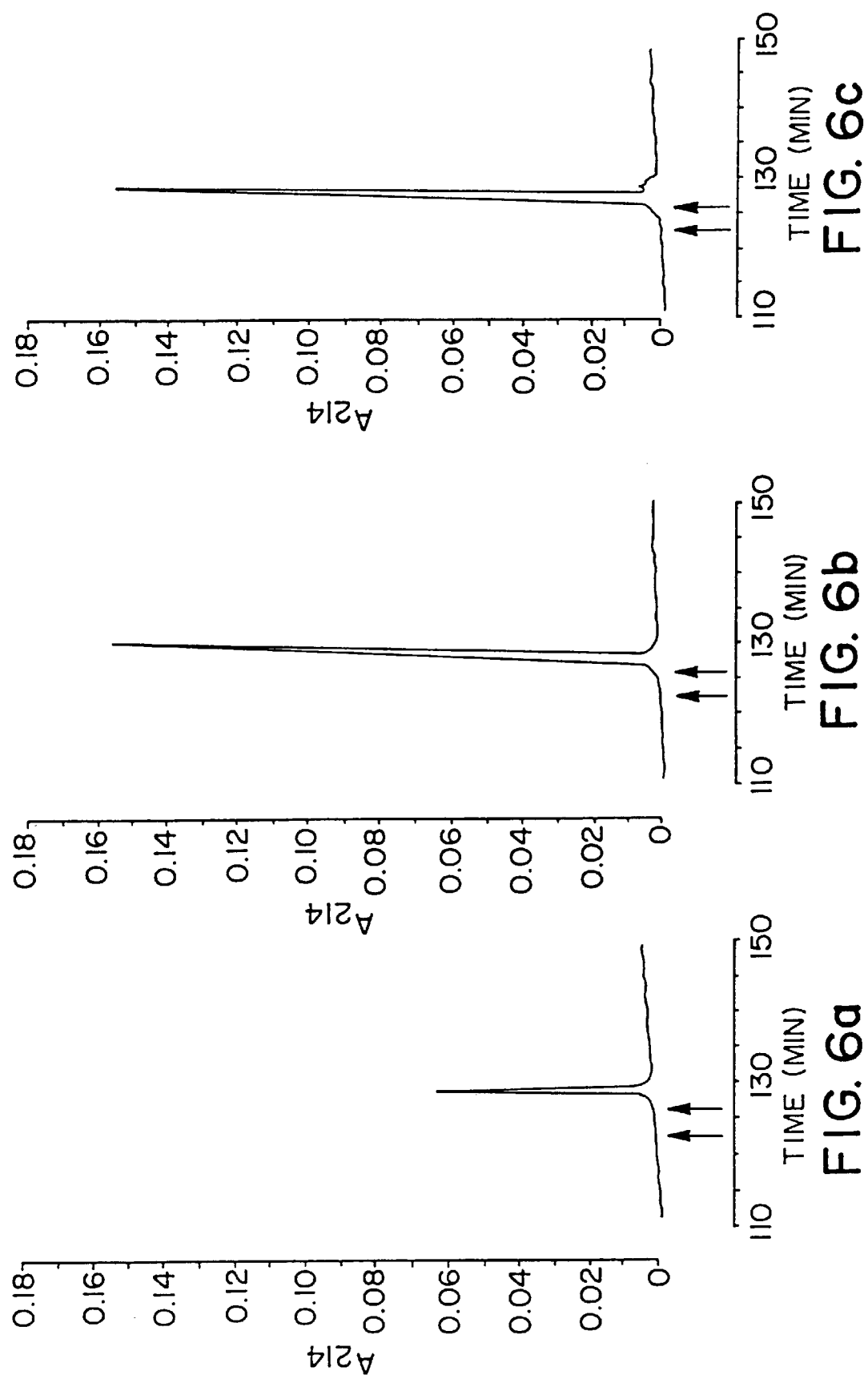
FIG. 6a–c (stability of the 12-mer hexa-oxime made with AOA-12-mer) shows chromatograms obtained during RP-HPLC of the hexa-TCTP-polyoxime following incubation for 48 hours at pH 2.16 (a), 24 hours at pH 4.656 (b) or 30.5 hours at pH 7.06 (c). Arrows indicate the expected elution times for incomplete penta-, tetra-, etc. TCTP polyoximes; no partial products are observed.

The molecular weight was determined more precisely by electrospray ionization mass spectrometry. The molecular mass of the product was measured to be 10,367.41+/−1.28 daltons (FIG. 5), which compares favorably with the predicted molecular weight of 10,365.49 daltons expected for the chemoselective ligation of six TCTP COSMs (SEQ ID NO: 4) to the hexa-GXL-baseplate structure (SEQ ID NO: 6).

The stability of the hexa-TCTP-polyoxime product was determined by incubating the hexaoxime (0. 1 mg/ml) at room temperature for 48 hours in 0.1% TFA (pH 2. 1), for 24 hours in 0.1 M sodium acetate (pH 4.6) or for 30.5 hours in phosphate buffered saline (pH 7.0). Following incubation, the samples were analyzed by RP-HPLC. As shown in FIG.

6, the hexa-TCTP-polyoxime was stable when incubated at the various pH values.

Example 4
Parallel Assembly Of Hexa-Pep C-polyoximes By Chemoselective Ligation Of A Hexa-GXL-baseplate And AOA-Pep C COSMS.

Figure 7:
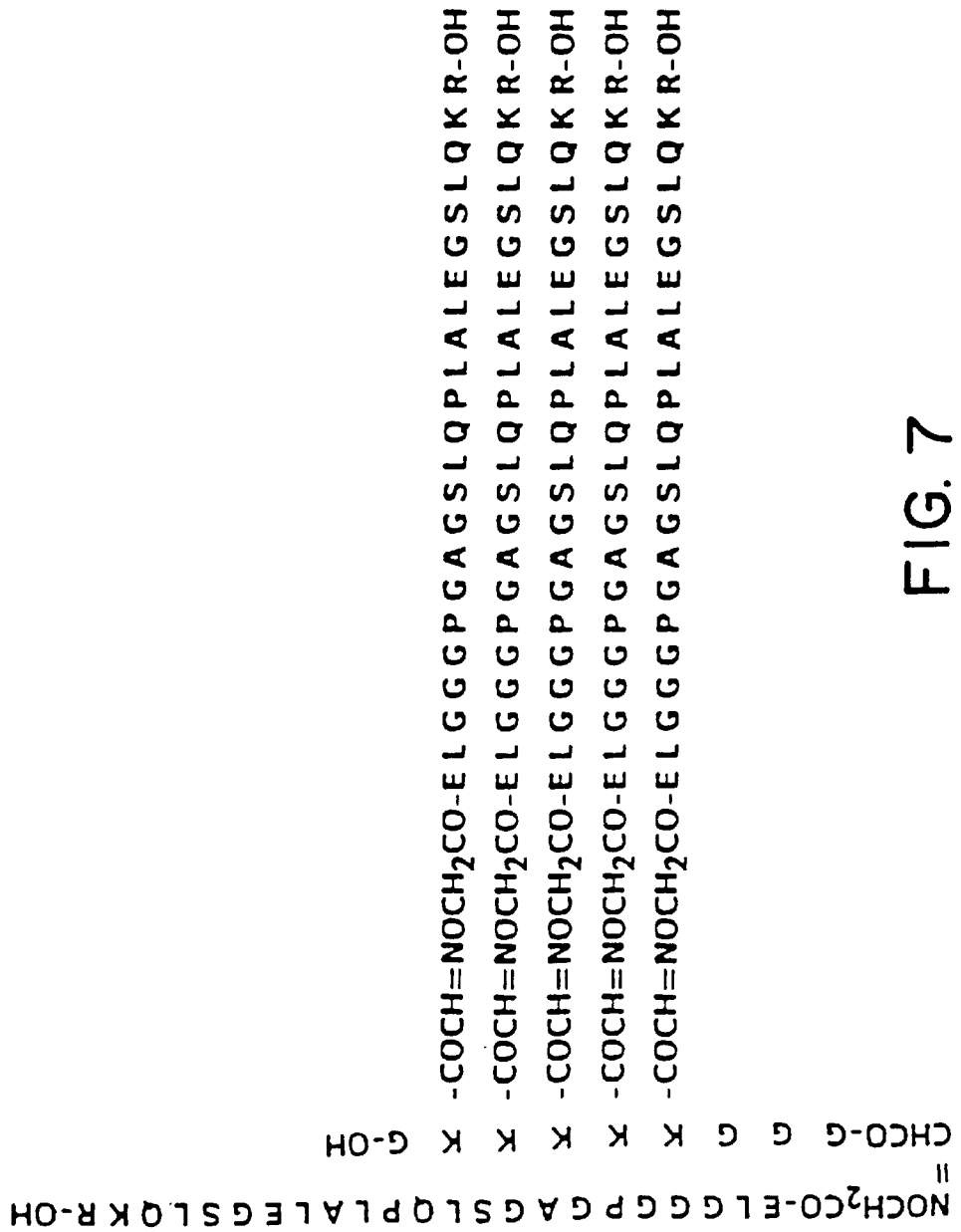
FIG. 7 depicts the structure of the hexa-Pep C-polyoxime. As indicated, a Pep C-COSM is attached to each of the five E-positions of the lysine residues in the baseplate structure and to the N-terminus of the baseplate structure.

Parallel assembly of the hexa-Pep C-polyoxime was initiated by adding 30 pi AOA-Pep C (10 mM in 01.M sodium acetate, pH 4.6) to 1 411 hexa-GXL-baseplate structure (10 mM in water) and incubating the mixture at room temperature. AOA-Pep C (SEQ ID NO: 10) was present in a five-fold molar excess of AOA groups over each GXL group on the baseplate structure (SEQ ID NO: 6). The structure of the expected hexa-Pep C-polyoxime is shown in FIG. 7.

Figure 8:
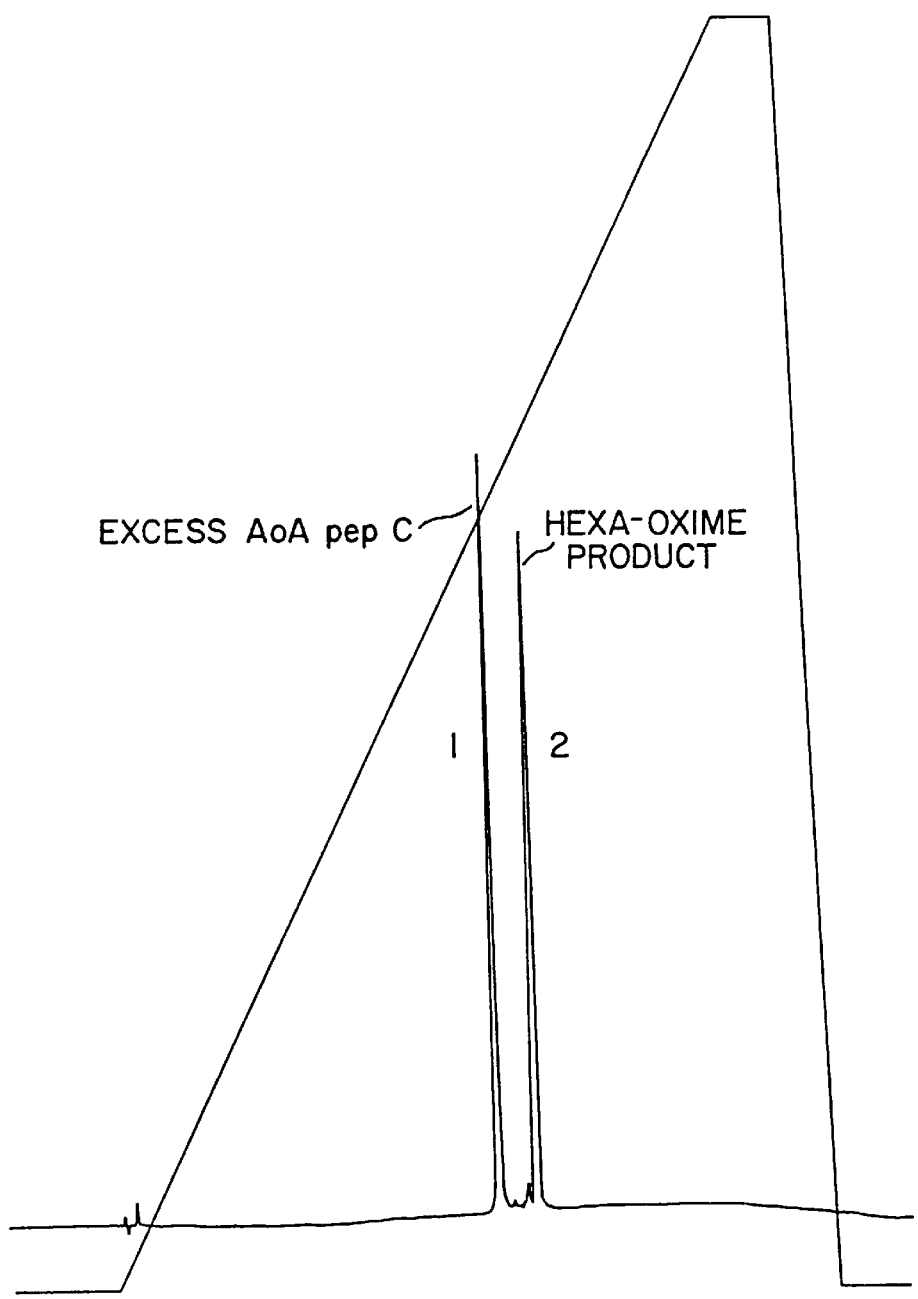
FIG. 8 shows the chromatogram obtained during RP-HPLC of sample taken 18 hours after beginning the oximation reaction. Peak 1 indicates the fraction containing unbound Pep C-COSM and Peak 2 indicates the fraction containing hexa-Pep C-polyoxime product.

The extent of chemoselective ligation was monitored by measuring the formation of the hexa-Pep C-polyoxime by RP-HPLC on the 4 mm id column. Elution was at 0.6 ml/min with 100% A for 5 min, followed by a gradient of 2% B/min to a final concentration of 100% B. FIG. 8 shows the chromatogram obtained after 18 hours of incubation. As was observed for the hexa-TCTP-polyoxime formation, hexa-Pep C-polyoxime formation was essentially complete after 18 hours of incubation. The reaction was terminated by performing preparative RP-HPLC as described in Example 3 above.

Figure 9:
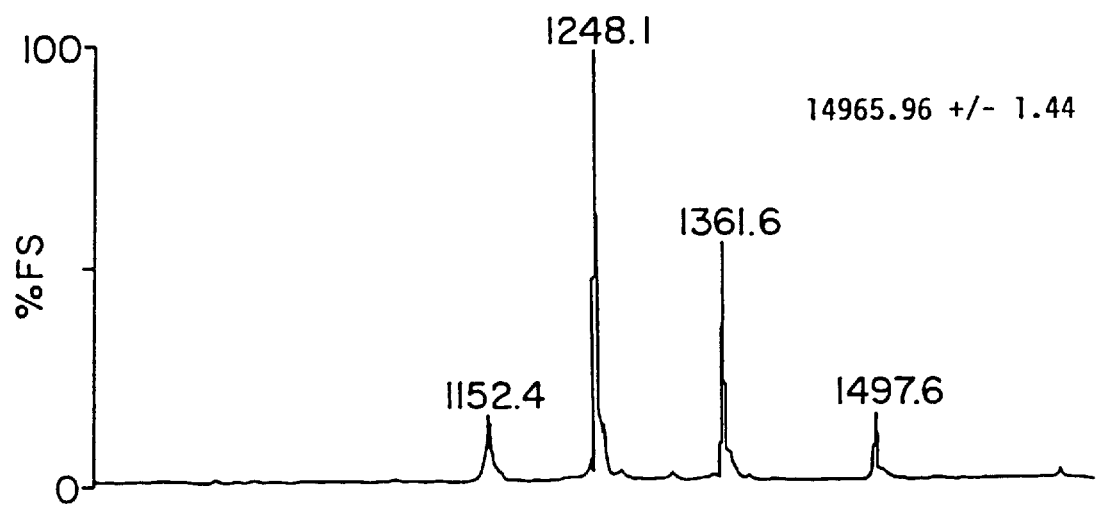
FIG. 9 (ESI-MS of the Pep C-hexaoxime) shows a mass spectrum obtained by electrospray ionization mass spectrometry of the hexa-Pep C-polyoxime.
Figure 10:
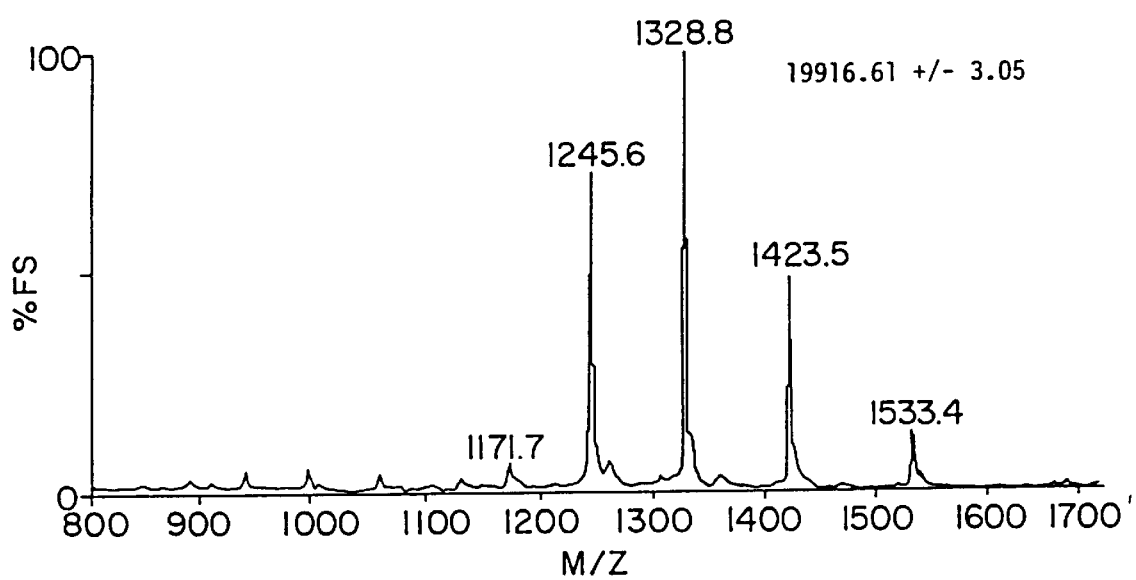
FIG. 10 (EST-MS of the Pep C-octaoxime) shows a mass spectrum obtained by electrospray ionization mass spectometry of an octa-Pep C-polyoxime.

Using electrospray ionization mass spectrometry, as described above, the molecular weight of the hexa-Pep C-polyoxime was measured to be 14,965.96+/−1.44 daltons as compared to be predicted value of 14,966.58 daltons for the ligation of six AOA-Pep C COSMs to the baseplate structure (SEQ ID NO: 6) (FIG. 9). For comparison, an electrospray ionization mass spectrum is shown from an experiment in which AOA-Pep C COSMs (SEQ ID NO: 10) were chemoselectively ligated to an octa-GXL-baseplate structure (SEQ ID NO: 9) (FIG. 10). Again, the measured value of 19916.61+/−3.05 daltons was comparable to the expected value of 19916.097 daltons for a polyoxime containing eight Pep C COSMs.

Example 5
Parallel Assembly Of Hexa-TCTP-polyoximes By Chemoselective Ligation Of A Hexa-AOA-baseplate And GXL-TCTP COSMS.

Figure 11:
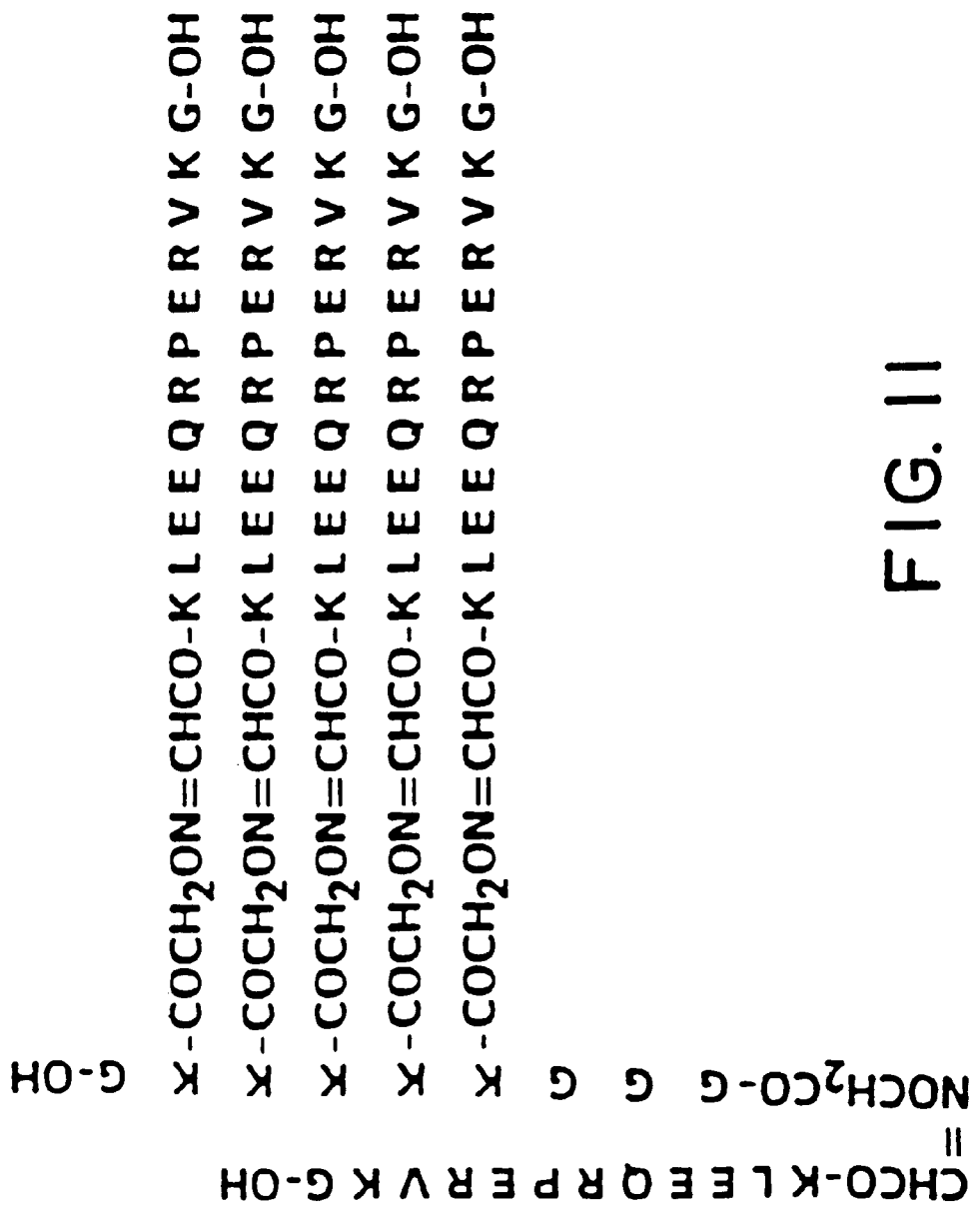
FIG. 11 depicts the structure of the hexa-TCTP-polyoxime. As indicated, a COSM is attached to each of the five e-positions of the of the lysine residues in the baseplate structure and to the N-terminus of the baseplate structure. Note the stereochemistry of the oxime bonds as compared to the structure shown in FIG. 1.

Parallel assembly of the hexa-TCTP-polyoxime was initiated by adding 1 µl hexa-AOA-baseplate structure (10 mM in water) to a mixture containing 180 µl 0.1 M sodium acetate buffer, pH 4.6, and 30 µl GXL-TCTP COSMs (SEQ ID NO: 3) (10 mM in water). The sample was mixed and incubated at room temperature. GXL-TCTP was present in a five-fold molar excess over each AOA group on the baseplate (SEQ ID NO: 5). The structure of the expected hexa-TCTP-polyoxime is shown in FIG. 11, which, except for the stereochemistry of the oxime bonds, is similar to the structure in FIG. 1.

The extent of chemoselective ligation was monitored by RP-HPLC, as described above, and formation of the hexa-TCTP-polyoxime was complete after 56 hours of incubation. No further change occurred during a 75 hour monitoring period. The reaction was terminated and hexa-TCTP-polyoxime product was purified by preparative RP-HPLC.

The molecular weight, as determined by electrospray ionization mass spectrometry, was measured to be 10,365.72 daltons as compared to the predicted molecular weight of 10,365.49 daltons expected for the ligation of six TCTP COSMs to the baseplate structure. The measured molecular weight also is very similar to the molecular weight of the labeled baseplate structure with AOA-COSMs. The resulting poly-COSM-oxime contains a amino terminal biotin or EDTA group.

Example 6
Preparation Of A Polyoxime Using A COSM Having A C-terminal Aldehyde.

The protease inhibitor, Leupeptin (Sigma Chem. Co), which contains a C-terminal aldehyde group, was chemoselectively ligated to a hexa-AOA-baseplate structure (SEQ ID NO: 5). Thirty µl of Leupeptin (10 mM in water) and 180 µl sodium acetate buffer (0.1 M, pH 4.6) was added to 1 µl of hexa-AOA baseplate (10 mM in water). After incubating the reaction for hours at room temperature, 20 µl of the reaction mixture was removed and analyzed by RP-HPLC using the standard gradient of 2% B/min from 0% to 100% B, as described in Example 1. The hexa-leupeptin-oxime eluted at a retention time 43 min. The mass of the hexa-leupeptinoxime was measured by electrospray mass spectrometry to be 3776.45±0.70 daltons, which compares favorably with the expected value of 3775.66 daltons.

Example 7
Immunization Using The Hexa-COSM-polyoxime.

About one hundred µg of the hexa-COSM-polyoxime, hexa-TCTP-polyoxime product, shown in FIG. 1, in complete Freund's adjuvant was injected subcutaneously into about 10 sites in each of a group of rabbits. At intervals of about 4–6 weeks, rabbits were given booster injections containing 50 µg hexa-COSM-polyoxime in incomplete Freund's adjuvant. About 10–14 days after a booster injection, rabbits were bled and the blood serum isolated. The serum contained cross-reactivity to the hexa-TCTP-polyoxime used as antigen. One skilled in the art would know that variations can be made in the amount of antigen used, the type of adjuvant, the site and method of injection and the timing of the injections (see, for example, Harlow and Lane (1988), chapter 5). Antiserum from hexa-TCTP-polyoxime immunized animals reacted with the antigen hexa-TCTP-polyoxime. The antiserum did not cross-react with TCTP protein in an immunoblot assay wherein TCTP protein was separated by two-dimensional SDS-PAGE and was probed with antiserum followed by labelled goat-anti-rabbit serum. Similarly, an octa-TCTP-MAP structure led to production of antibodies against the octa-TCTP-MAP (MAP is "Multiple Antigenic Peptide as disclosed by Tam and Zavala (1989)), which did not cross-react with TCTP protein, but in contrast to the hexa-TCTP-polyoxime gave an artifact by cross-reacting with the β-chain of haptoglobin in the immunoblot assay. Antibodies can be detected by using, for example, an immunodot blot assay and purified using methods well known in the art (see, for example, Harlow and Lane (1988), pages 178–179 and chapter 8).

Example 8
Preparation Of A Polyoxime Having A Signal-producing Group.

Signal-producing groups are attached to a COSM or to the baseplate structure either prior to or following the oximation reaction. An N-hydroxysuccinimide ester of biotin or Boc-biocytin N-hydroxysuccinimide ester is coupled to the a-amino group of H-Gly$_3$[Lys(Boc-Ser(benzyl)]$_5$-Gly-PAM resin using the standard conditions for peptide synthesis described above. Alternatively, a chelator group such as Fmoc-Lys (EDTA penta-t-butyl ester)—H is coupled to a α-amino group of the baseplate structure using methods well known in the art (see, for example, Rana et al., Tetrahedron Lett. 33:45214524 (1992), which is incorporated herein by reference). Neither biotin nor EDTA is damaged by the cleavage-deprotection reaction, by the oxidation reaction to the GXL-baseplate or by the oximation reaction of the labeled baseplate structure with AOA-COSMs. The resulting poly-COSM-oxime contains a amino terminal biotin or EDTA group.

Example 9
Attachment Of Polyoximes To A Solid Surface.

In order to attach a polyoxime to a solid surface chemoselective ligation can be used. For example, a polyoxime can be attached to a surface using thiol chemistry. Bromoacetyl-Gly$_3$-[Lys(Ser)]$_5$Gly-OH is made by standard solid phase peptide synthesis, oxidized to the penta-GXL-baseplate (SEQ ID NO: 8), oximated with AOA-COSMs and purified by RP-HPLC, as described above.

Thiol groups are attached to surfaces using methods that are known in the art. A solid material containing aminopropyl groups on its surface is first acylated by treatment with S-acetylthioacetic acid N-hydroxysuccinimide ester. The acylated surface is then treated with dilute aqueous hydrqxylamine to deacylate and expose the reactive thiol groups. The bromoacetyl-polyoxime is coupled to the thiol groups on the solid surface by formation of a thioether bond under mild aqueous conditions at pH 4–9. Preferably, thioether formation is performed at pH 6.5–7.5 (see, for example, Brinkley, M., *Bioconj. Chem.* 3:2–13 (1992), which is incorporated herein by reference). Unbound material is removed by washing the surface.

Example 10
Cell-cell Attachment Mediated By Linked Polyoximes.

Two different types of polyoximes are synthesized using the methods described above. One type of polyoxime contains COSMs that recognize and attach to a tumor antigen. The other type of polyoxime contains COSMs that recognize and attach to a cell surface receptor present, for example, on a macrophage, T cell or killer cell. The two types of polyoximes are constructed such that the C-termini or the N-termini of the baseplate structures have complementary orthogonal chemically reactive groups, such as a sulfhydryl group and bromoacetyl group.

The two types of polyoximes can then be covalently linked by thioether formation under mild aqueous conditions at pH 4–9. Preferably, thioether formation is performed at pH 6.5–7.5. Following completion of the reaction, the bi-polyoximes are purified by standard methods such as gel filtration or IRP-HPLC and are used to mediate cell attachment between cells containing the appropriate receptors or target molecules, such as a macrophage, T cell or killer cell and a tumor cell. Such bi-polyoximes are used to localize effector cells, such as those described above, to a target cell of interest, such as a tumor cell.

One skilled in the art would know that many different cell surface receptors and target molecules have been identified on different types of cells. Accordingly, the bi-polyoximes are constructed so as to mediate attachment of the particular cells of interest.

One skilled in the art would also recognize that bi-polyoximes can contain one type of COSM that recognizes and binds to a particular cell and a second type of COSM that is useful, for example, for binding a reporter molecule. Such bi-polyoximes are useful for detecting the presence and location of the particular cell in a heterogeneous population of cells or in an animal. Alternatively, the second type of COSM can bind an effector molecule, such as ricin, thereby directing the effector molecule to the particular cell of interest.

Example 11
Parallel Assembly Of Various Melanocyte Stimulating Hormone Analog-polyoximes.

Synthetic polypeptides NH$_2$OCH$_2$ CO-Nle-Asp-His-(D-Phe)-Arg-Trp-Lys-OH and NH2OCH2CO-Nle-Asp-His-(D-Pbe)-Arg-Trp-Lys-amide (both alpha-melanocyte stimulating hormone ("MSH") analogs) carrying an N-terminal aminooxyacetyl group were prepared and separately incubated with a poly(aldehyde) baseplate molecule, e.g. terephthalaldehyde or OCH-CO-Gly$_3$-[Lys(COCHO)]$_5$-Gly-OH (SEQ ID NO: 6), in aqueous solution in acetate buffer, pH 4.6, at room temperature. The oximation reactions were followed by reversed phase HPLC as described. Reactions with di-and tri-valent aldehyde baseplates were rapid (1 h) while reactions with hexa- or octa-valent aldehyde baseplates took longer (about 16 h) but nevertheless proceeded close to completion. The final product was in each case characterized by mass spectrometry. All experimentally determined masses were in excellent agreement with the calculated values. NH2OCH2CO-Nle-Asp-His-D-Phe)-Arg-Trp-Lys-OH and NH2OCH2CO-Nle-Asp-H is-(D-Phe)-Arg-Trp-Lys-amide reacted smoothly with terephthalaldehyde to give the homodimers p-C6H4[CH=NOCH2CO-Nle-Asp-H is-(D-Phe)-Arg-Trp-Lys-OH]2 and p-C6H4[CH=NOCH2CO-Nle-Asp-His-(D-Phe)-Arg-Trp-Lys-amide]2. ESI-MS of the —OH form is shown in FIG. 12B. Products were generally highly water-soluble, although this property will clearly depend on the hydrophilicity of the components used. Isomeric species were made by reversing the polarity of the oxime bond.

HPLC analysis showed polyoximes to be hydrolytically stable at room temperature at pH 2.1, 4.6 and 7.0 over at least 24 hours. Oxime bond hydrolytic stability, which was found to be influenced by its structure, was observed to increase in the series: —CO—NH—CH2—CH=N—O—CH2<—NH—CO—CH=N—O—CH2—<—C6H4—CH=N—O—CH2—. The stability of an oxime bond in vivo is thus sufficient to allow biodistribution studies of an immunoconjugate to be followed over several days in mice and also in the clinic. Of course, these artificial proteins would be expected to be subject to deamidation, oxidation, microbial degradation, etc. as are natural polypeptides and proteins.

Example 12
Synthesis Of A Divalent And A Trivalent Aldehyde Baseplate.

Nitriloacetic acid (Fluka, 64 mg, 1 mmol carboxyl groups) was dissolved with sonication and slight warming in 15 ml DMF. 1 mmol N-hydroxy-succinimide solid (Fluka) was added and dissolved, then 1 ml of 1 M dicyclohexyl-carbodiimide (Fluka) added. After overnight reaction at room temperature no DCC remained and the reaction was filtered to remove some DCC urea precipitate. To the filtrate was added 1.2 mmol aminoacetaldehyde diethylacetal (Fluka). After overnight reaction, 30 ml 0. 1% trifluoroacetic acid was added followed by 1 ml 0.1% TFA in 90% acetonitrile and then 0.6 ml acetic acid. After thorough mixing, DCC urea was again removed by filtration through a Teflon membrane filter. The product was purified in 10 ml portions by preparative HPLC using the 250×20 mm column already described, monitoring at 214 nm and running at 6 ml/min with the TFA system. After 5 min with solvent A (0.1% TFA), a linear gradient of 2% B/min was applied (B=0.1% TFA in 90% acetonitrile). The retention time of the trivalent acetal N[CH2—CO—NH—CH2—CH(OEt)2]$_3$ was 42 min and that of the divalent acetal N[CH2—CO—NH—CH2—CH(OEt)2]$_2$CH2—CO2H was 35 min. The products were identified by FAB-MS: mrz 537 for M+H$^+$ of the trivalent acetal and 422 for M+H$^+$ of the divalent acetal.

After removal of solvents on the rotary evaporator and by lyophilization, deacetalization was effected with 5% TFA at 37° C. for 2 h. The trialdehyde decomposed if the 5% TFA solution was directly evaporated, so instead product N[CH2—CO—NH—CH2—CHO], was isolated by injecting small (30 μl) portions on the preparative column operated at 6 ml/min isocratically with solvent A, washing the column with 100% B between injections. The excess TFA from the deprotection eluted with retention time 11 min and the product tri-aldehyde baseplate eluted at 13 min. The tri-aldehyde solution was adjusted to pH about 3 with 1 M NaOH and stored at −20 C. The divalent aldehyde baseplate was similarly isolated.

Example 13
Preparation Of Asymmetrical Divalent And Symmetrical Trivalent Polyoximes.

Oximation between the trivalent, symmetrical baseplate N[CH2—CO—NH—CH2—CHO]$_3$ and the amino-oxy-acetyl-alpha-MSH free acid analog of Example 11 were carried out as previously described. Mono-, di- and tri-oximes were prepared. These eluted from analytical HPLC (250×4 mm id column, 0.6 ml/min, 2% B/min gradient) with retention times of 32, 35 and 36 min, respectively.

Example 14
Synthesis Of An Acetyl-Cysteine Baseplate.

Fmoc-Cys(Trt)-OSu 0.2 mmol in 20 ml dry DMSO was added to 0.1 mmol H-Gly3-Lys[Boc-Ser(Bzl)-]5-Gly-OCH2-PAM-resin. "OSu" indicates the N-hydroxysuccinimide ester form. After a few hours mixing at an apparent pH of 8 (adjusted with N-methyl morpholine), acylation was complete as determined by a ninhydrin test. Fmoc was removed using DMF/piperidine and the resulting free amino group was acetylated with 5 equivalents of acetic anhydride in DMF using N-methyl morpholine as base. Cleavage/deprotection was as follows: to 100 mg resin was added 150 ul thioanisolelethane-dithiol (2:1 by vol.); after 10 min stirring at room temperature, 1 ml TFA was added and stirring continued for 10 min; then 100 ul TFMSA (trifluoromethane sulfonic acid) was added slowly with vigorous mixing and the reaction allowed to proceed for 25 min with stirring; cold diethyl ether (10 ml) was then added to precipitate the peptide; after 1 min stirring, the precipitate was recovered by centrifugation along with the now-cleaved resin; crude peptide was dissolved in 0.5 ml TFA, filtered to remove resin through a Teflon filter, then precipitated again with cold ether. Product was purified by HPLC on a 250×4 mm id column operated at 0.6 ml/min with the TFA system, 1% B/min after an initial 5 min at 100% A. The product eluted as a major peak at retention time 25 min and was characterized by ESI-MS (found 1467.92+/−0.79; calculated 1466.62).

Example 15
Preparation Of Hetero-Polyoximes.

By limiting the amount of modified peptide added to a multivalent baseplate, partial reaction products were rapidly formed and easily isolated. For example, NH$_2$OCH$_2$CO-Nle-Asp-His-(D-Phe)-Arg-Trp-Lys-OH reacted smoothly with a five-fold excess of terephthalaldehyde (10-fold excess of aldehyde groups) to give OCH—C$_6$H$_4$—p—CH=NOCH$_2$ CO-Nle-Asp-His-(D-Phe)-Arg-Trp-Lys-OH, which was isolated by HPLC and characterized by ESI-MS (FIG. 12A). Reaction of this mono-oxime with a slight excess of NH$_2$OCH$_2$CO-Lys-Leu-Glu-Glu-Gln-Arg-Pro-Glu-Arg-Val-Lys-Gly-OH (SEQ ID NO: 4) led rapidly to the expected heterodimeric oxime, p-C$_6$H$_4$ [CH=NOCH$_2$CO-Nle-Asp-His-(D-Phe)-Arg-Trp-Lys-OH] [CH=NOCH$_2$CO-Lys-Leu-Glu-Glu-Gln-Arg-Pro-Glu-Arg-Val-Lys-Gly-OH], which was characterized by ESI-MS (FIG. 12C). A similar heterodimer was made using NH$_2$OCH$_2$CO-Lys-Leu-Glu-Gln-Arg-Pro-Glu-Arg-Val-Lys-Gly-OH (SEQ ID NO: 13) in place of NH$_2$OCH$_2$CO-Lys-Leu-Glu-Glu-Gln-Arg-Pro-Glu-Arg-Val-Lys-Gly-OH (SEQ ID NO: 4) and was also characterized by ESI-MS (FIG. 12D).

Example 16
Attachment of a Complementary Reactive Group to a Peptide Cysteine Side Chain by Alkylation and Subsequent Polyoxime Formation Compounds (i) Br—CH2—CO—NHCH2CH2NH—CO—CH2—O—NH—Boc, and (ii) Br—CH2—CO—NHCH2CH2NH—CO—CH2—O—NH2 were synthesized as follows. To ten mmol Boc—NHOCH2CO—OSu dissolved in 85 ml ethyl acetate was added 1.35 ml (20 mmol) ethylenediamine, with mixing. After one hour at room temperature, a precipitate was removed by centrifugation followed by solvent removal by rotary evaporation without heating. The resulting sticky residue was taken up in 20 ml 1% acetic acid. A small amount of insoluble dimeric material was removed at this stage by centrifugation. The aqueous solution was cooled in ice, then applied to a Dowex-50W×8 200–400 mesh column (in H+form) previously equilibrated with water, packed in a 10 ml disposable polypropylene syringe and cooled in ice. Ice was used to reduce the loss of Boc protecting group upon liberation of protons by the resin during sample binding. The Dowex column was eluted at a flow rate of about 0.5 ml/min with a gradient of pyridine acetate buffer made by connecting a 40 ml chamber of pH 3.5 buffer (pyridine/acetic acid/water, 10:100:890 by vol.) with a 40 ml chamber of pH 6.5 buffer (pyridine/acetic acid/water, 250:10:2250 by volume) and drawing from the pH 3.5 chamber.

Column effluent was monitored by TLC on silica plates using a butan-1-ol/acetic acid/water/acetone (7:2:4:7 by volume) system followed by staining with ninhydrin. The intermediate compound (iii) NH2CH2CH2NH—CO—CH2—O—NH—Boc was the first ninhydrin positive material to emerge (Rf was about 0.7 in the above system; de-Boc material Rf was about 0.4; ethylenediamine Rf was about 0.07). After solvent removal by rotary evaporation without heat, the residue was diluted with water and freeze dried to a colorless oil. Final purification was by preparative reversed phase HPLC on the 20 mm diameter column, TFA system, 5 ml/min, 10 min isocratic 100%A, followed by a linear gradient of solvent B to 100%B over 15 min, with monitoring at 229 nm. Wanted material was the only major peak after the solvent front and had a retention time of about 33 min. The intermediate was identified as (iii) by electrospray ionization mass spectrometry.

To 250 mg BrCH2CO—OSu dissolved in 2 ml DMSO was added with mixing a solution of 110 mg compound (iii) dissolved in 1 ml DMSO. The apparent pH (measured with a Merck pH indicator strip previously moistened with water) was brought to about 8 by addition of 50 ul N-methylmorpholine. After 20 min (the pH fell to about 4) 25 ml water was added. A small precipitate was removed by filtration, and product was isolated by RP-HPLC as before. In this case the sample was applied in portions of about 8 ml. After a 5 min isocratic period at 100% A, a linear gradient of 2% B/min was applied with monitoring at 229 nm. Product was the only major peak after appearance of the solvent front and had a retention time of about 41 min. Product was isolated by rotary evaporation followed by freeze drying. Yield was about 100 mg. The material, characterized as compound (i) by electrospray ionization mass spectrometry, had the expected bromine isotope pattern around M+H 355.

Compound (ii) was prepared by removing the Boc group of compound (i) by dissolving the latter at 50 mg/ml in trifluoroacetic acid for 30 min at room temperature followed by drying under high vacuum.

Compounds (i) and (ii) were taken up in water at 40 and 50 mg/ml, respectively, for alkylation. The peptide acetyl-Asp-Cys-Thr-Leu-Ile-Asp-Ala-Leu-Leu-Gly-Asp-Pro-His-amide (SEQ ID NO: 20; a T-cell epitope of influenza virus; see Brown et al., *J. Virol.* (1993) 67:2887–2893) was made by standard Fmoc techniques on an ABI 430A synthesizer, purified by reversed phase HPLC and identified by electrospray ionization mass spectrometry: mass found and calculated was 1423.6. The peptide was dissolved at 1.5 mM in water/acetonitrile (2:1 v/v). To 100 ul 0.1% trifluoroacetic acid was added 20 ul peptide solution, 20 ul reagent solution (Compound (i) or (ii)) and 20 ul 1 M phosphate buffer (counter ion sodium, pH 7.0). Reactions were carried out at room temperature. Analytical reversed phase HPLC with the TFA system showed quantitative reaction within 30 min with both Compounds (i) and (ii): the unreacted peptide (retention time 39 min) was absent and replaced by a new peak at either retention time 37 min (in the case of reaction with compound (ii)) or 41 min (in the case of reaction with compound (i)). No further reaction took place over the next 3 hours. In the absence of reagents (i) or (ii), the peptide slowly oxidized to the disulfide dimer (about 30% over 6 hours). The products of the alkylation reactions were identified by electrospray ionization mass spectrometry: for the product with reagent (i), mass found was 1697.0, calculated was 1696.9; for the product with reagent (ii), mass found was 1596.6, calculated was 1596.8.

In the case of polypeptides alkylated with compound (i), the Boc group was removed by standard TFA treatment prior to oximation. Polypeptides alkylated with compound (ii) did not require this treatment. Reagent (i) is recommended where the alkylated peptide must be stored for long periods of time, while reagent (ii) is recommended for use with large or fragile polypeptides (such as antibody fragments) which do not easily survive intact treatment to remove the Boc group.

Another alkylating reagent Br—$CH_2CH_2CH_2NH$—$COCH_2ONH$—Boc was prepared by acylation of Br—$CH_2CH_2CH_2NH_2$ (available as the hydrobromide from Aldrich, Milwaukee, Wis.) with Boc-AOA-OSu. This alkyl halide was used to alkylate the Cys-containing influenza virus peptide described above. Reactions occurred very slowly at room temperature even with millimolar concentrations.

Example 17
Parallel Assembly of Peptides having Thioether Linked Aminooxyacetyl Complementary Reactive Groups.

The polypeptides carrying a free aminooxyacetyl group attached to a Cys side chain through a thioether link were used in oximation reactions as described above for polypeptides carrying an aminooxyacetyl group on the N- or C-terminus. This provides a method for producing polyoximes having a COSM connected to a baseplate via a Cys side-chain through thioether and oxime bonds. The polypeptide derivatives of Example 16 were used with baseplates described herein to create various polyoximes. For example, the tetra-oxime between acetyl-Asp-Cys(CH2CONH—CH2CH2NH—COCH2ONH2)—Thr-Leu-Ile-Asp-Ala-Leu-Leu-Gly-Asp-Pro-His-amide (SEQ ID NO: 21) and the baseplate GXL-Lys(GXL)-Lys(GXL-Lys(GXL))-TyrOH (SEQ ID NO: 31) can be formed. The baseplate was formed by the steps of coupling Fmoc-Lys(Fmoc) to Tyr(tBu)-Sasrin resin, deFmoc, recoupling Fmoc-Lys(Fmoc), deFmoc, coupling Boc-Ser(tBu), cleavage/deprotection, and oxidation of Ser to GXL. AOA-Lys(AOA)-Lys(AOA-Lys(AOA))-Tyr—OH was also made.

Example 18
Attachment of a reactive group to the side chain of cysteine through a disulfide bond.

Compounds (iv) 2-pyridyl—S—S—CH2CH2NH—CO—CH2—O—NH—Boc and (v) 2-pyridyl—S—S—CH2CH2NH—CO—CH2—O—NH2 were synthesized as follows. Cystamine dihydrochloride was acylated in DMF with Boc—NHOCH2CO—OSu using N-methylmorpholine as base and a 20% excess of active ester over amino groups. After dilution with three volumes of water, acylated product was extracted into ethyl acetate and purified on a silica gel column using dichloromethane/methanol (240:10) as solvent. The product, bis(Boc-amninooxyacetyl) cystamine, was a single peak on analytical HPLC and had the expected mass spectrum. The disulfide bond was reduced with a five-fold excess of dithiothreitol in 1% ammonium bicarbonate solution and the resulting Boc-aninooxyacetyl-cysteamine isolated by preparative HPLC. The thiol group was reacted with 2,2'-dithiodipyridine (5-fold excess in 0.1 M sodium acetate buffer, pH 4.6) to give compound (iv), which was isolated (along with excess reagent) by extraction with diethylether. Addition of a small proportion of petroleum ether precipitated most of the excess reagent, leaving compound (iv) in solution. After rotary evaporation compound (iv) was purified by HPLC and characterized by electrospray ionization mass spectrometry (M+H 360.5). Transformation of compound (iv) to compound (v) was achieved by standard treatment with TFA (one hour, room temperature).

Compounds (iv) and (v) reacted cleanly via the 2-thiopyridyl group with Cys-containing peptides, under mild aqueous conditions (e.g. acetate buffer pH 4.6 or phosphate buffer pH 7 with low millimolar concentrations of reagents at 22° C.; reaction was complete after 10 min). For example, compounds (iv) and (v) were reacted with peptides acetyl-Asp-Cys-Thr-Leu-Ile-Asp-Ala-Leu-Leu-Gly-Asp-Pro—H is-amide and AOA-Asp-Cys-Thr-Leu-le-Asp-Ala-Leu-Leu-Gly-Asp-Pro-His-amide (SEQ ID NO: 22). Acetyl-Asp-Cys(S—CH2CH2NHCOCH2ONH-Boc)-Thr-Leu-Ile-Asp-Ala-Leu-Leu-Gly-Asp-Pro-H is-amide (SEQ ID NO: 30) was purified by RP-HPLC and characterized by electrosprav ionization mass spectrometry: mass found, 1671.7, mass calculated, 1671.9. Cys includes its S atom by convention, so that, for example, Cys(S—CH2CH2NHCOCH2ONH—Boc) in the above structure indicates a disulfide bond containing side chain formed between the S atom of Cys and the S atom of S—CH2CH2NHCOCH2ONH—Boc. This convention is followed throughout. The resulting peptide derivatives possessed an aminooxyacetyl (or protected aminooxyacetyl) group attached through a disulfide bond.

The aminooxyacetyl group and the dithiopyridyl group may be present on the same peptide COSM. For example, $NH_2OCH_2CO$—Asp-Cys(S—2-pyridyl)-Thr-Leu-Ile-Asp-Ala-Leu-Leu-Gly-Asp-Pro-$NH_2$ (SEQ ID NO: 23) was made by reacting the —SH form of the AOA-peptide with 2,2'-dithiodipyridine (at pH 4.6 under conditions described above). The modified peptide was isolated by HPLC and gave the expected electrospray ionization mass spectrum. This peptide COSM was reacted, in a mixture of 0.1M acetate buffer (counter ion sodium) and acetonitrile (2:1 v/v) with a tetraaldehyde baseplate that was made as follows. The baseplate was constructed based on the cyclic structure described by Mutter (Tuchscherer et al., in Peptides 1992, Schneider, C. H. and Eberle, A. N., eds., ESCOM, Leiden, (1993) pp 848–849) which has a disulfide bond between the two Cys (C) residues: Ac-Cys-Lys-Ala-Lys-Pro-Gly-Lys-Ala-Lys-Cys-NH2 (SEQ ID NO: 24). The four Lys (K) side chains of this template precursor were acylated with Boc-Ser(tBu)—OSu under standard conditions. The acylated product was isolated by HPLC and Boc and butyl protection was removed by treatment with TFA at room temperature for one hour. TFA was removed under vacuum without heating. The resulting baseplate precursor, which gave a single peak on analytical HPLC and the expected electrospray ionization mass spectrum, was oxidized with periodate as described for the previous baseplates and was reisolated by HPLC. After 16 hours of oximation at room temperature, the expected tetraoxime was isolated by HPLC and characterized by electrospray ionization mass spectrometry: mass found was 7479.31, calculated was 7479.43. The polyoxime eluted from the analytical column after 45 minutes when using a 2%B/min gradient from 0 to 100% B.

As determined herein, the presence of the 2-thiopyridyl protecting group on the Cys side chains did not prevent oxime formation.

Example 19
COSMS As Linkers

The COSMs as prepared herein can themselves be used as linkers. For example, the AOA-COSM $NH_2OCH_2CO$—Asp-Cys(S—2-pyridyl)-Thr-Leu-Mle-Asp-Ala-Leu-Leu-Gly-Asp-Pro-His-$NH_2$ (SEQ ID NO: 23), which possesses both AOA and 2-thiopyridyl functions, was used as a linker to create the following COSM having a disulfide bond between the two Cys residues:

Example 20
Synthesis of a Trivalent Baseplate with Aromatic Aldehyde Groups.

The baseplate

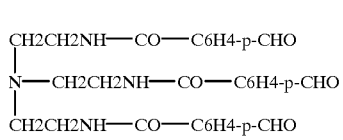

(vi)

was synthesized as follows. Fifty ul tris(2-aminoethyl)amine (about 1/3 mmol; Aldrich Chemical Co.) was dissolved in 5 ml DMSO and added to 4-carboxybenzaldehyde hydroxysuccinimide ester (247 mg, 1 mmol, dissolved in 5 mnl DMSO). After 2 h at room temperature, 20 ml water was added. After a further 2 h, product was extracted with 2×10 ml chloroform. The pooled organic phase was washed with 10 ml water then taken to dryness by rotary evaporation. The pale yellow solid was sonicated in 50 ml water, filtered, and dried under high vacuum to afford 94 mg slightly off-white powder. The product eluted as a single major component on reversed phase HPLC and was identified as (vi) by electrospray ionization mass spectrometry: mass found and calc. 542 (543 M+H). A small (less than 10%) contaminant visible on the HPLC trace was identified as (vi) lacking one 4-carboxybenzaldehyde group (M+H 411), i.e. the baseplate:

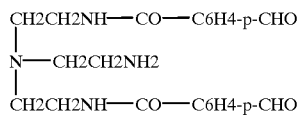

(vii)

For some applications, this contaminant was removed by preparative HPLC. By using more tris(2-aminoethyl)amine in the above acylation reaction (and the same amount of active ester), the production of (vii) was favored as expected, and it was easily isolated by preparative HPLC using the TFA system.

For compounds (vi) and (vii), the para-substitution employed is expected to give the least steric hindrance for the acylation reaction and for subsequent oxime formation. The central nitrogen atom of these structures assures water solubility; even the trialdehyde is soluble at the millimolar concentrations employed.

Preferred linkers are those that have complementary reactive end groups as taught herein, provide homogeneity of reaction product (except when a homologous series is used as discussed below), and provide other functionality (e.g. solubility or desired three dimensional conformation) but does not interfere with the desired reactions (be it alkylation, disulfide formation or oxime formation).

Example 21
Polyoximes Prepared Using Aromatic Aldehyde Templates.

Polyoximes were made using the aromatic tri- and di-aldehyde templates (vi) and (vii), including oximes with the aminooxyacetylated peptides as described above (for example with the analog of alpha-MSH:AOA-Nle-Asp-His-(D)Phe-Arg-Trp-Lys-amide). Reactions were followed by RP-HPLC and electrospray ionization mass spectrometry. The polyoximes were purified by HPLC and characterized by electrospray ionization mass spectrometry: all had the expected mass. Compounds (vi) and (vii) were found to form oximes which were particularly resistant to hydrolysis and also resistant to reduction with sodium cyanoborohydride (0.3 M) in acetic acid (0.33 M).

It is known that the alpha-MSH analogue Nle-Asp-His-(D-Phe)-Arg-Trp-Lys binds to melanoma cells even when modified at the alpha-amino group and when linked as a homodimer through this group (Bagutti et al. Prog. Histochem. Cytochem. (1992) 26:110–118). The biological activity of MSH can be measured, for example, with an in situ melanin assay in which the peptide is tested for stimulation of B16-F1 melanoma cells (Bagutti 1992).

The binding and potency of some alpha-melanocyte stimulating hormone analog polyoximes were determined. Relative binding in the binding assay using mouse melanoma cells (Bagutti (1992)) refers to the average dissociation constant (Kd) for full-length natural hormone divided by the Kd for our oxime analog. Relative potency in the melanin assay (Bagutti (1992)) refers to the ratio of the concentrations (giving 50% of maximum effect) of full-length hormone and that of analog. Results with the analog of alpha-MSH, Nle-Asp-His-(D)Phe-Arg-Trp-Lys-amide, are provided. The control monooxime of this analog (aminooxyacetyl peptide oximated with acetaldehyde) had relative binding of 0.82 and relative potency of 1.78. The trioxime formed between the aminooxyacetyl peptide and compound (vi) had a relative binding of 4.9 and a relative potency of 0.24. The dioxime formed between the aminooxyacetyl peptide and glyoxal (O═CH—CH═O) had a relative binding of 3.33 and a relative potency of 3.15

Example 22
Alkylation of Antibody Fragments and Subsequent Polyoxime Formation.

Compound (ii) was also used to alkylate much larger polypeptides, including F(ab') fragments of IgG antibodies produced by reduction of the disulfide bonds which link the heavy chains of F(ab')2 fragments. F(ab') fragments of the monoclonal antibody Mab35 were prepared by standard means. The peptic F(ab')$_2$ was reduced with cysteamine to the F(ab')SH, which was then alkylated with reagent (ii) and oximated either with baseplate (vi) or (vii) below. Reactions were followed (with and without full reduction with 10 mM dithiothreitol prior to analysis) by SDS-PAGE, gel filtration chromatography and electrospray ionization mass spectrometry. The expected dioxime was formed in good yield, and the trioxime in lower yield (probably for reasons for steric hindrance: such hindrance is usually lesser when longer linkers are used). In vivo the F(ab')$_2$ polyoxime will have reduced localization in the kidneys resulting in a reduced rate of excretion.

Example 23
Reduction of the Oxime Bond.

Reduced oxime bonds are less sensitive to hydrolysis at neutral and acidic pH than the non-conjugated aliphatic oxime. Reduction of the oxime bond was done according to a procedure in the Comprehensive Organic Synthesis, Barry M. Trost, ed. in chief, Vol. 8, Ian Fleming, ed., pp 60–78, Pergamon Press, Oxford, 1991. Oximes formed between non-conjugated aliphatic groups, e.g. —CH2—CH=NO—CH2—, were easily reduced at room temperature within minutes to very few hours with 0.3 M sodium cyanoborohydride in 0.33 M acetic acid. Prolonged treatment (e.g. overnight) led to decomposition. The reduced product eluted earlier on reversed phase HPLC than unreduced starting material and was identified by electrospray ionization mass spectrometry, which confirmed the expected increase of two mass units per oxime bond reduced. The reduced oxime (now an N,O-dialkylhydroxylamine) was less sensitive to hydrolysis at neutral and acidic pH than the non-conjugated aliphatic oxime.

Conjugated aliphatic oximes, e.g. —NH—CO—CH=NO—CH2—, could only be partially reduced upon prolonged treatment with reducing agent. Aromatic oximes, e.g. —C6H4—CH=NO—CH2—, could not be reduced under these conditions. Stronger conditions are known (see e.g. Comprehensive Organic Synthesis, Barry M. Trost, ed. in chief, Vol. 8, Ian Fleming, ed., pp 60–78, Pergamon Press, Oxford, 1991) which will reduce such oximes and may be useful in some circumstances, although care has to be taken not to reduce other sensitive groups present, such as the indole side chain of tryptophan.

Example 24
Immunogenic Polyoximes.

The T-cell epitope of influenza virus peptide H-Asp-Cys-Thr-Leu-Ile-Asp-Ala-Leu-Leu-Gly-Asp-Pro-His-NH2. (Brown et al., J. Virol. (1993) 67:2887–2893) and the B- and T-epitope containing C-terminal peptide H-Pro-Lys-Tyr-Val-Lys-Gln-Asn-Thr-Leu-Lys-Leu-Ala-Thr-Gly-Met-Arg-Asn-Val-Pro-Glu-Lys-Gln-Thr-OH (SEQ ID NO: 25; e.g. Jackson, D. C. and Brown, L. E., Peptide Research (1991) 4:114–124) were used to exemplify the making of polyoxime immunogens.

The peptide AOA-Pro-Lys-Tyr-Val-Lys-Gln-Asn-Thr-Leu-Lys-Leu-Ala-Thr-Gly-Met-rg-Asn-Val-Pro-Gll-Lys-Gln-Thr—OH (SEQ ID NO. 26) was made by automated solid phase ynthesis on an ABI 430A machine using standard Fmoc protocols and commercially available Fmoc-Thr (tBu)-Sasrin resin (from Bachem, AG, 144 Hauptstrasse, 4416 Bubendorf, Switzerland). Prior to cleavage and deprotection, the peptide was acylated on the resin with Boc—NHOCH2CO—OSu and worked up as described above. After purification by preparative HPLC, the peptide was characterized by electrospray ionization mass spectrometry both as the free aminooxyacetyl peptide and as the oxime formed by incubation of a portion at pH 4.6 with a small excess of acetaldehyde and isolation by HPLC of the product. The mass of the acetaldehyde oxime was 2744.46 found and 2744.18 calculated.

The cyclic baseplate described above that was based on Ac-Cys-Lys-Ala-Lys-Pro-Gly-Lys-Ala-Lys-Cys-NH2 was used for polyoxime formation. It was oxidized with periodate as described and isolated by HPLC. Parallel assembly oximation was then carried out between the glyoxylyl groups (created by oxidation of Ser groups on the Lys (K) side chains) and the aminooxyacetyl group of the peptide AOA-Pro-Lys-Tyr-Val-Lys-Gln-Asn-Thr-Leu-Lys-Leu-Ala-Thr-Gly-Met-Arg-Asn-Val-Pro-Glu-Lys-Gln-Thr-OH, under the conditions described above (acetate buffer pH 4.6, 5-fold excess of peptide over each glyoxylyl group, 16 h, room temperature). The resulting tetraoxime was isolated by HPLC and characterized by electrospray ionization mass spectrometry (found 12097.08, calculated 12097.04).

The polyoxime, in this case a tetraoxime, was tested in the T-cell proliferation assay and, also in vivo in mice for protection against viral challenge.

Using the methods described herein the following COSMs, useful for immunogenicity, were also made: AOA-Asp-Cys-Thr-Leu-Ile-Asp-Ala-Leu-Leu-Gly-Asp-Pro-His-NH2 (SEQ ID NO: 22), Ac-Asp-Cys(CH2CH2CH2NH-AOA)-Thr-Leu-Ile-Asp-Ala-Leu-Leu-Gly-Asp-Pro-His-NH2 (SEQ ID NO: 27), Ac-Asp-Cys (CH2CONHCH2CH2NH—AOA)-Thr-Leu-le-Asp-Ala-Leu-Leu-Gly-Asp-Pro-His-NH2 (SEQ ID NO: 21), and

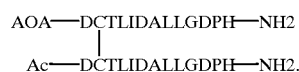

Other useful COSMs are: Ac-Asp-Cys*-Thr-Leu-lle-Asp-Ala-Leu-Leu-Gly-Asp-Pro-His—NHCH2CH2NH—AOA (SEQ ID NO: 28) where Cys* is the S-carboxamidomethyl derivative of Cys, Ac-Asp-Cys-Thr-Leu-Ile-Asp-Ala-Leu-Leu-Gly-Asp-Pro—His-NHCH2CH2NH-AOA (SEQ ID NO: 29), and

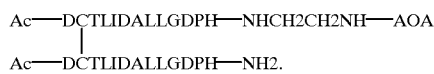

A heterotetraoxime immunogenic polyoxime is exemplified by having two copies of both AOA-Asp-Cys*-Thr-Leu-Ile-Asp-Ala-Leu-Leu-Gly-Asp-Pro-His-NH2 and AOA-Pro-Lys-Tyr-Val-Lys-Gln-Asn-Thr-Leu-Lys-Leu-Ala-Thr-Gly-Met-Arg-Asn-Val-Pro-Glu-Lys-Gln-Thr-OH, where Cys* is the S-carboxamidomethyl derivative of Cys.

Example 25
Polyoxime Homologous Series.

The use of aminooxyacetyl- (or aldehyde-modified-) monomethoxy-polyethyleneglycol, or other homologous series of polymers as COSM mixture, allows a polyoxime to have heterogeniety within the molecule itself. Such polyoximes are formed by parallel assembly of a mixture of members of a homologous series such as: NH₂OCH₂CO—NH—CH₂CH₂O(CH₂CH₂O)ₙCH₂CH₂CH₂CH₃ or O—CHCH₂O(CH₂CH₂O)ₙCH₂CH₂OCH₃ or O=CHCONHCH₂CH₂O(CH₂CH₂O)ₙCH₂CH₂OCH₃, where n is an integer. Aldehydic- and AOA-modified molecules of a homologous series can be used in parallel assembly polyoxime formation.

The present invention now provides the means to synthesize rapidly polyoxime multirmers of biological compounds for screening, such as MSH, having varying spacing, charge, lipophilicity, valency, conformational restraints, solubility and other desirable physical and biological (e.g immunological) properties.

Although the invention has been described with reference to the above-provided embodiments, it should be understood that various modifications can be made without departing from the scope and spirit of the invention. Accordingly, the scope of the invention is limited only by the following claims.

We claim:

1. A homogeneous homopolyoxime composition, in which homopolyoxime molecules present in said composition comprise a first organic baseplate molecule linked via a plurality of at least three oxime linkages to a plurality of second organic molecules, said oxime linkages being formed by reaction of an orthogonal reactive group on each said second organic molecule with a complementary orthogonal reactive group on said baseplate, wherein said orthogonal reactive group and said complementary orthogonal reactive group are selected from the group consisting of an aldehyde group, a keto group and an amino-oxy group, as appropriate for complementarity, wherein said second organic molecules are identical in structure, said orthogonal reactive groups on second organic molecules are identical to each other, and said at least three complementary orthogonal reactive groups on said baseplate are identical to each other.

2. A homogeneous hetero-polyoxime composition, wherein said heteropolyoxime molecules present in said composition comprise a first organic baseplate molecule linked via a plurality of at least three oxime linkages to a plurality of second organic molecules, said oxime linkages being formed by reaction of an orthogonal reactive group on each said second organic molecule with a complementary orthogonal reactive group on said baseplate, wherein said orthogonal reactive group and said complementary orthogonal reactive group are selected from the group consisting of an aldehyde group, a keto group and an amino-oxy group as appropriate for complementarity, and wherein at least one of said second organic molecules attached to said baseplate is different from another second organic molecule attached to said baseplate.

3. The composition of claim 1 or claim 2, wherein said second organic molecule is a therapeutic agent or a detectable marker.

4. The composition of claim 1 or claim 2, wherein said composition is immunogenic.

5. A pharmaceutical composition, comprising the composition of claim 1 or claim 2 and a pharmaceutically acceptable carrier.

6. A method of inducing an immune response in an animal, which comprises administering to said animal an immunologically effective amount of the pharmaceutical composition of claim 5, wherein said homopolyoxime molecule or said heteropolyoxime molecule is immunogenic and is present in an immunologically effective amount.

7. A method of imaging a cell, comprising contacting the cell with a detectable amount of the composition of claim 1, wherein the homopolyoxime molecule further comprises a detectable marker or an imaging agent linked to the baseplate, under conditions in which the formation of a complex between the imaging agent or detectable marker and the target cell occurs, and detecting any complex so formed.

8. A homogeneous homopolyoxime composition prepared by a process comprising the steps of:
   1) obtaining a first organic baseplate molecule having present therein a plurality of at least three identical orthogonal reactive groups capable of oxime linkage formation, wherein said orthogonal reactive groups are amino-oxy groups, aldehyde groups or keto groups;
   2) obtaining a second organic molecule having present therein a complementary orthogonal reactive group capable of oxime linkage formation with said orthogonal reactive group on said baseplate molecule, wherein said complementary orthogonal reactive groups are amino-oxy groups, aldehyde groups or keto groups, as appropriate for complementarity;
   3) contacting said baseplate molecule with an amount of said second organic molecule sufficient for essentially complete reaction between said second organic molecule and said plurality of orthogonal reactive groups on said baseplate molecule under conditions allowing oxime linkage formation, whereby oxime linkage formation occurs between the orthogonal reactive groups on said baseplate and the complementary orthogonal reactive groups on said second organic molecules; and
   4) separating the homopolyoxime product from unreacted second organic molecules.

9. A method of producing a homogeneous homopolyoxime composition, comprising the steps of:
   1) obtaining a first organic baseplate molecule having present therein a plurality of at least three identical orthogonal reactive groups capable of oxime linkage formation, wherein said orthogonal reactive groups are amino-oxy groups, aldehyde groups or keto groups;
   2) obtaining a second organic molecule having present therein a complementary orthogonal reactive group capable of oxime linkage formation with said orthogonal reactive group on said baseplate molecule, wherein said complementary orthogonal reactive groups are amino-oxy groups aldehyde groups or keto groups as appropriate for complementarity;
   3) contacting said baseplate molecule with an amount of said second organic molecule sufficient for essentially complete reaction between said second organic molecule and said plurality of orthogonal reactive groups on said baseplate molecule under conditions allowing oxime linkage formation, whereby oxime linkage formation occurs between the orthogonal reactive groups on said baseplate and the complementary orthogonal reactive groups on said second organic molecules; and
   4) separating the homopolyoxime product from unreacted second organic molecules.

10. A homogeneous hetero-polyoxime composition produced by a process comprising the steps of:
   1) obtaining a first organic baseplate molecule having present therein a plurality of at least three orthogonal reactive groups capable of oxime linkage formation, wherein said at least three orthogonal reactive groups are independently selected from the group consisting of an aldehyde group, a keto group, an amino-oxy group and protected forms thereof;
   2) obtaining a second organic molecule having present therein an orthogonal reactive group, selected from the group consisting of an aldehyde group, a keto group and an amino-oxy group, capable of oxime linkage formation with its complementary orthogonal reactive group on the baseplate;
   3) obtaining a third organic molecule having present therein an orthogonal reactive group, selected from the group consisting of an aldehyde group, a keto group and an amino-oxy group, capable of oxime linkage formation with its complementary orthogonal reactive group on the baseplate, wherein said second organic molecule and said third organic molecule are different in structure;
   4) mixing the baseplate and the second organic molecules under conditions allowing oxime linkage formation, whereby oxime linkage formation occurs with said second organic molecule in the same position or positions in each baseplate molecule;
   5) mixing the baseplate and the third organic molecules, either contemporaneously or sequentially with said mixing in step 4), under conditions allowing oxime linkage formation, whereby oxime linkage formation occurs with said third organic molecule in the same position or positions in each baseplate molecule; and
   6) separating the hetero-polyoxime product from unreacted second and third organic molecules.

11. A method of producing a homogeneous heteropolyoxime composition comprising the steps of:
   1) obtaining a first organic baseplate molecule having present therein a plurality of at least three orthogonal reactive groups capable of oxime linkage formation, wherein said at least three orthogonal reactive groups are independently selected from the group consisting of an aldehyde group, a keto group, an amino-oxy group and protected forms thereof;
   2) obtaining a second organic molecule having present therein an orthogonal reactive group, selected from the group consisting of an aldehyde group, a keto group and an amino-oxy group, capable of oxime linkage formation with its complementary orthogonal reactive group on the baseplate;
   3) obtaining a third organic molecule having present therein an orthogonal reactive group, selected from the group consisting of an aldehyde group, a keto group and an amino-oxy group, capable of oxime linkage formation with its complementary orthogonal reactive group on the baseplate, wherein said second organic molecule and said third organic molecule are different in structure;

4) mixing the baseplate and the second organic molecules under conditions allowing oxime linkage formation, whereby oxime linkage formation occurs with said second organic molecule in the same position or positions in each baseplate molecule;

5) mixing the baseplate and the third organic molecules, either contemporaneously or sequentially with said mixing in step 4), under conditions allowing oxime linkage formation, whereby oxime linkage formation occurs with said third organic molecule in the same position or positions in each baseplate molecule; and 6) separating the hetero-polyoxime product from unreacted second and third organic molecules.

12. The composition of claim 1 or claim 2 wherein said first organic baseplate molecule and said second organic molecules comprise amino acid residues.

13. The composition of claim 8 wherein said first organic baseplate molecule and said second organic molecule comprise amino acid residues.

14. The composition of claim 10 wherein said first organic baseplate molecule, said second organic molecule and said third organic molecule comprise amino acid residues.

15. The method of claim 9 wherein said first organic baseplate molecule and said second organic molecule comprise amino acid residues.

16. The method of claim 11 wherein said first organic baseplate molecule, said second organic molecule and said third organic molecule comprise amino acid residues.

17. A method of imaging a cell, comprising contacting the cell with a detectable amount of the composition of claim 2, wherein the heteropolyoxime molecule further comprises a detectable marker or an imaging agent linked to the baseplate, under conditions in which the formation of a complex between the imaging agent or detectable marker and the target cell occurs, and detecting any complex so formed.

* * * * *